(12) United States Patent
Duvold

(10) Patent No.: US 6,673,783 B2
(45) Date of Patent: Jan. 6, 2004

(54) FUSIDIC ACID DERIVATIVES

(75) Inventor: Tore Duvold, Frederiksberg (DK)

(73) Assignee: Leo Pharmaceutical Products Ltd. A/S, Ballerup (DK)

( * ) Notice: Subject to any disclaimer, the term of this patent is extended or adjusted under 35 U.S.C. 154(b) by 0 days.

(21) Appl. No.: 10/091,580

(22) Filed: Mar. 7, 2002

(65) Prior Publication Data

US 2003/0064971 A1 Apr. 3, 2003

Related U.S. Application Data

(60) Provisional application No. 60/273,950, filed on Mar. 8, 2001.

(51) Int. Cl.[7] .......................... A61K 31/56; C07J 31/00; C07J 13/00
(52) U.S. Cl. ....................... 514/182; 552/525; 552/523; 552/530; 552/531
(58) Field of Search ................................. 552/525, 523, 552/530, 531; 514/182

(56) References Cited

U.S. PATENT DOCUMENTS 4,548,922 A * 10/1985 Carey et al. ................... 514/4
4,746,508 A * 5/1988 Carey et al. .................. 424/88
4,959,358 A * 9/1990 Carey et al. ................ 514/171

OTHER PUBLICATIONS

Bodley et al. (DN 76:136239, HCAPLUS, abstract of Biochem. Biophys. Res. Commun. (1972), 46(2), 871–7).*
Prehn et al. (DN 68:74913, HCAPLUS, abstract of Acta Pathol. Microbiol. Scand. (1967), 71(1), 135–40).*

* cited by examiner

Primary Examiner—Sabiha Qazi
(74) Attorney, Agent, or Firm—Birch, Stewart, Kolasch & Birch, LLP

(57) ABSTRACT

Novel 17,20-methanofusidic acid derivatives are used in pharmaceutical compositions for the treatment of infections, in particular in topical compositions for the treatment of skin or eye infections.

19 Claims, No Drawings

FUSIDIC ACID DERIVATIVES

This application claims the benefit of Provisional Application No. 60/273,950 filed Mar. 8, 2001.

FIELD OF THE INVENTION

The present invention relates to novel fusidic acid derivatives, to salts and to easily hydrolysable esters thereof, to the preparation of these compounds, to pharmaceutical compositions containing the compounds and to the use of such compounds in medicine. In particular, these compounds exhibit antimicrobial activity and are therefore useful in the treatment of infectious diseases. The compounds of the present invention can be used both in systemic treatment of infections and in topical treatment of infections related to skin and eyes.

BACKGROUND OF THE INVENTION

The antibacterial properties of fusidic acid are well known. It is also known that structural variations may cause significant or total loss of such activity (cf. Godtfredsen et al, *J. Med. Chem.*, Vol. 9, p. 15–22, 1966). It has until now been generally accepted that the double bond between the carbon atoms C-17 and C-20 which connect the side-chain to the tetracyclic ring system is essential for any antibacterial activity (cf. Bodley and Godtfredsen, *Biochem. Biophys. Res. Commun.* 46, 1972, pp. 871–877). Reduction of the double bond between C-24 and C-25 of fusidic acid to a single bond resulted in a marginal effect on the antibacterial activity of the molecule whereas additional reduction of the double bond between C-17 and C-20 yielding tetrahydrofusidic acid caused almost complete loss of activity (cf. von Daehne et al., *Adv. Appl. Microbiol.*, 25, p. 95–146,1979, and references cited therein).

SUMMARY OF THE INVENTION

The object of the present invention is to provide semi-synthetic analogues of fusidic acid having antimicrobial activity. Said object is achieved with the compounds of the present invention that belong to a class of fusidic acid derivatives in which the side chain is connected to the tetracyclic ring system at C-17 via a fused cyclopropane ring and which in vitro show high antimicrobial activity and favourable stability and pharmacokinetic properties, whereby the compounds of the invention may be used in treatment of infections in humans and animals.

The present invention relates to compounds of the general formula I

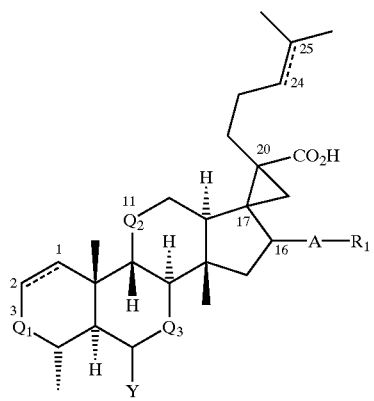

wherein $Q_1$, $Q_2$ and $Q_3$ are the same or different and independently represent a —(CO)— group; a —(CHOH)— group; a —(CHOR)— group; a —(CHSH)— group; a —(NH)— group; a —(CHNH$_2$)— group; a —(C—X)— group, wherein X represents halogen; or a —(CHNHR)— group, wherein R represents an alkyl radical having 1 to 4 carbon atoms or an acyl radical having 1 to 4 carbon atoms; and wherein $Q_2$ and $Q_3$ may also independently represent a —(CH$_2$)— group;

Y represents hydrogen, hydroxy, an alkyl radical having 1 to 4 carbon atoms, or an acyl radical having 1 to 4 carbon atoms;

A represents an oxygen or a sulphur atom;

$R_1$ represents an alkyl radical having 1 to 4 carbon atoms, an olefinic group having 2 to 4 carbon atoms, a ($C_1$–$C_6$) acyl group, ($C_3$–$C_7$)cycloalkylcarbonyl group or a benzoyl group $R_1$ being optionally substituted with one or more halogen at azido groups;

and pharmaceutically acceptable salts and easily hydrolysable esters thereof.

In formula I and subsequent formulas herein the dotted lines between C-1 and C-2 and between C-24 and C-25 indicate that the atoms in question are connected with either a double bond or a single bond.

It has surprisingly been found that compounds of formula I exhibit an excellent chemical stability relative to fusidic acid and derivatives thereof which have a carbon-carbon double bond between C-17 and C-20. The superior stability may be due to the absence of Conjugation of the carboxylic acid with a carbon-carbon double bond. The presence of a cyclopropane ring in this position is therefore expected to impart to the present fusidic acid derivatives an improved stability in the presence of light and in solution. As the compounds of formula I are more lipophilic than fusidic acid, they may exhibit an improved absorption profile in lipophilic tissue such as skin, and may therefore be particularly advantageous for incorporation into used in topical formulations for application on skin. Furthermore, as the pH value of the compounds of formula I may be neutral or approximately neutral, skin irritation problems following topical application may substantially be avoided.

DETAILED DESCRIPTION OF THE INVENTION

Preferred compounds of the invention are compounds of formula Ia

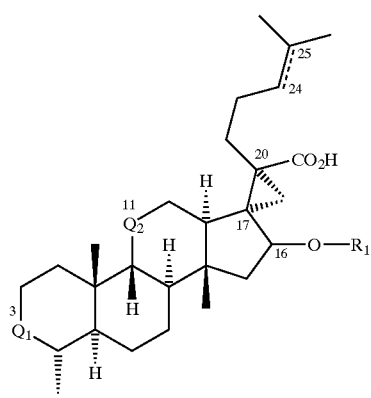

Ia wherein $Q_1$ and $Q_2$ are the same or different and independently represent a —(CHOH)— group; a —(CO)— group, or a —(CHSH)— group, or wherein $Q_1$ is a group

wherein X is halogen;

$R_1$ represents an alkyl radical having 1 to 4 carbon atoms, an olefinic group having 2 to 4 carbon atoms, a ($C_1$–$C_6$) acyl group, a $C_1$–$C_7$cycloalkylcarbonyl group or a benzoyl group, $R_1$ being optionally substituted with one or more halogen atoms and/or hydroxy, alkoxy or azido groups;

and pharmaceutically acceptable salts and easily hydrolysable esters thereof.

Preferably $Q_1$ and $Q_2$ are selected from the group consisting of —(CO)— and —(CHOH)—. More preferred compounds of the invention are compounds of formula I or Ia wherein $Q_1$ and $Q_2$ both represent a

group; or one of $Q_1$ or $Q_2$ represents —(CO)—; A represents oxygen; $R_1$ represents a ($C_1$–$C_4$)alkyl group, optionally substituted with one or more substituents selected from the group consisting of azido, hydroxy, and halogen selected from fluoro, chloro and bromo, or $R_1$ represents an acyl group with 1 to 4 carbon atoms or a benzoyl group, both optionally substituted with one or more halogen atoms, preferably selected from the group consisting of fluoro and chloro. $R_1$ is preferably selected from the group consisting of ethyl, 2,2,2-trifluoroethyl, 2,2,2-trichloroethyl, 2-azidoethyl, 2-hydroxyethyl, propyl, tert.-butyl, isopropyl, 1,3-difluoro-isopropyl, acetyl, propionyl, chloroacetyl and trifluoroacetyl, or $R_1$ is selected from the preferred group consisting of ethyl, 2,2,2-trichloroethyl, 2-azidoethyl, isopropyl, tert-butyl and acetyl. Also preferred are compounds of formula I and Ia wherein the bond between C-24 and C-25 is a double bond.

Examples of compounds of the invention which can all be prepared by the methods described below are:

17S,20S-Methanofusidic acid, Compound 101
24,25-Dihydro-17S,20S-methanofusidic acid, Compound 102
11-Dehydro-17S,20S-methanofusidic acid, Compound 103
3-Dehydro-17S,20S-methanofusidic acid, Compound 104
16-Deacetoxy-16β-propionyloxy-17S,20S-methanofusidic acid, Compound 105
16-Deacetoxy-16β-cyclohexylcarbonyloxy-17S,20S-methanofusidic acid, Compound 106
16-Deacetoxy-16β-(isopropionyloxy)-17S,20S-methanofusidic acid, Compound 107
16-Deacetoxy-16β-(4'-fluorobenzoyloxy)-17S,20S-methanofusidic acid, Compound 108
16-Deacetoxy-16β-furfuryloxy-17S,20S-methanofusidic acid, Compound 109
16-Deacetoxy-16β-ethoxy-17S,20S-methanofusidic acid, Compound 110
16-Deacetoxy-16β-(1',1',1'-trifluoroethoxy)-17S,20S-methanofusidic acid, Compound 111
16-Deacetoxy-16β-methoxymethyl-17S,20S-methanofusidic acid, Compound 112
3-Dehydro-3β-bromo-17S,20S-methanofusidic acid, Compound 113
3-Dehydro-3β-chloro-17S,20S-methanofusidic acid, Compound 114 and pharmaceutically acceptable salts and easily hydrolysable esters thereof.

In contrast to natural fusidic acid (1) wherein C-17 and C-20 are connected with a double bond, all compounds described herein and by formula I and Ia have a cyclopropane ring between C-17 and C-20. The configuration of the two asymmetric carbon atoms in question is 17(S) and 20(S).

The compounds of the invention can be used as such or in the form of salts or easily hydrolysable esters (as hereinafter defined). The salts of the compounds are especially the pharmaceutically acceptable salts, such as alkali metal salts and alkaline earth metal salts, for example sodium, potassium, magnesium or calcium salts, as well as silver salts and salts with bases, such as ammonia or suitable non-toxic amines, such as lower alkylamines, for example triethylamine, hydroxy-lower alkylamines, for example 2-hydroxyethylamine, bis-(2-hydroxyethyl)-amine, cycloalkylamines, for example dicyclohexylamine, or benzylamines, for example N,N'-dibenzylethylenediamine, and dibenzylamine. The silver salts of the compounds are especially useful for local treatment.

The expression "easily hydrolysable esters" is used in this specification to denote alkanoyloxyalkyl, aralkanoyloxyalkyl, aroyloxyalkyl, for example acetoxymethyl, pivaloyloxymethyl, benzoyloxymethyl esters and the corresponding 1'-oxyethyl derivatives, or aikoxycarbonyloxyalkyl esters, for example methoxycarbonyloxymethyl esters and ethoxycarbonyloxymethyl esters, and the corresponding 1'-oxyethyl derivatives, or lactonyl esters, for example phthalidyl esters, or dialkylaminoalkyl esters, for example diethylaminoethyl esters. The expression "easily hydrolysable esters" includes in vivo hydrolysable esters of the compounds of the invention, Such esters may be prepared using methods known to a skilled person in the art, cf. GB patent No. 1 490 852 hereby incorporated by reference.

As used in the specification, unless specified to the contrary, the following terms have the meanings indicated, cf. also IUPAC Recommendations 1994 http://www.chem.qmw.ac.uk/iupac/class/.

"Alkyl" refers to any univalent group derived from an alkane by removal of a hydrogen atom from any carbon atom, and includes the subclasses of primary, secondary and tertiary alkyl groups respectively, and having the number of carbon atoms specified, including for example $(C_1-C_4)$alkyl, $(C_1-C_3)$alkyl, $(C_1-C_2)$alkyl, methyl, ethyl, n-propyl, isopropyl, n-butyl, isobutyl, sec-butyl, and t-butyl. Alkane refers to an acyclic branched or unbranched hydrocarbon having the general formula $C_nH_{2n+2}$, where n represents an integer, and therefore consisting entirely of hydrogen atoms and saturated carbon atoms.

"Olefinic group" refers to a straight or branched acyclic hydrocarbon having one or more carbon-carbon double bonds of either E or Z stereochemistry where applicable, and having the number of carbon atoms specified. The term includes, for example, $(C_2-C_4)$olefinic group, preferably a $(C_2-C_4)$alkenyl; $(C_2-C_3)$olefinic group, preferably a $(C_2-C_3)$alkenyl; vinyl; allyl; 1-butenyl; 2-butenyl; and 2-methyl-2-propenyl. Further, "alkynyl" refers to a straight or branched alkynyl moiety having at least one triple bond. This term would include, for example, crotyl and propargyl. Olefinic groups having only one carbon-carbon double bond, herein called alkenyl, are preferred.

"Aryl" refers to groups derived from monocyclic and polycyclic aromatic hydrocarbons by removal of a hydrogen atom from a ring carbon atom, e.g. o-tolyl, phenyl, naphthyl. The number of carbon atom in an aryl group is typically 6, 7, 8, 9 or 10.

"Acyl" refers broadly to a radical of the formula R—CO—, where R is alkyl as defined above, for example $(C_1-C_6)$acyl.

"Alkoxy" refers broadly to a radical of the formula —OR, where R is alkyl as defined above, for example $(C_1-C_5)$alkoxy, $(C_1-C_3)$alkoxy, methoxy, n-propoxy, t-butoxy, and the like.

"Halogen" means the same or different of fluoro, chloro, bromo, and iodo; fluoro, chloro, and bromo being more useful in the present compounds.

"Alkanoyl" refers broadly to a radical of the formula —R—CO—, where R is alkyl as defined above, for example $(C_1-C_8)$alkanoyl, acetyl, propionyl, isopropionyl, butyryl. "Aralkanoyl" refers broadly to a radical of the formula —R(CH$_2$)$_n$—CO—, wherein R is aryl as defined above and n is an integer, preferably selected from 1, 2, 3, and 4. "Aroyl" refers broadly to R—CO— where R is an aryl group as defined above.

"Alkanoyloxyalkyl" or "aroyloxyalkyl" refer broadly to a radical of the formula —CH$_2$—O—CO—R, wherein R represents a $(C_1-C_6)$alkyl group or a $(C_6-C_8)$aryl group. Aryl and alkyl are as defined above.

"Alkoxycarbonyl-" and "aryloxycarbonyl-" refer to the group —CO—OR or "acyloxy-" refers to the group R—CO—O— wherein R is alkyl or aryl as defined above.

There are several chiral centres in the compounds according to the invention because of the presence of asymmetric carbon atoms. The presence of several asymmetric carbon atoms gives rise to a number of stereoisomers with R or S configuration at each chiral centre. General formula I and Ia, and (unless specified otherwise) all other formulae in this specification are to be understood to include all such stereoisomers in pure form and as mixtures (for example stereoisomeric mixtures) except where the configuration is expressly indicated.

In the compounds of formula I and Ia, the preferred stereochemistry is in general as follows: when $Q_1$ and $Q_2$ refer to the

group the configuration at C-3 and C-11 in the compounds of formula I and Ia is 3α and 11α, respectively. When $Q_1$ is the group group

the configuration at C-3 may be either α or β. The C-16 atom carrying the A group has the (S)— configuration, hereinafter denoted 16β. In the formulas herein plain lines depict bonds which can be above or below the plane of the drawing; bonds to atoms above the plane are shown with a bold wedge starting from an atom in the plane of the drawing at the narrow end of the wedge; and bonds to atoms below the plane are shown with short parallel (wedged) lines. Substituents above the plane are described as β and shown as a bold wedge, those below the plane are described as α and shown by a line with short parallel (wedged) lines.

Biological Activity

In vitro investigations have evidenced high potency of compounds of the invention against several bacteria including Staphylococci, Streptococci, Corynebacteriae, Mycobacteriae and Neisseriae. Biological tests have showed comparable antibacterial activity of 17S,20S-methanofusidic acid (Compound 101) to that of fusidic acid (1) as can be seen from Table 1 showing MIC values of the two mentioned compounds and four other potent compounds of formula Ia towards a number of bacterial strains. The potency of new fusidic acid analogues are estimated by comparing the inhibition of growth of different microorganisms produced by known concentrations of the analogue to be examined and a reference like fusidic acid. The microbiological assay set up is in agreement with the European Pharmacopoeia 3rd edition (1997). It is an agar diffusion method where the same volume of the tested solution is added to cavities in agar. The inhibition zones are function of the concentration of the fusidic acid analogue used. All assays are run with fusidic acid as reference substance.

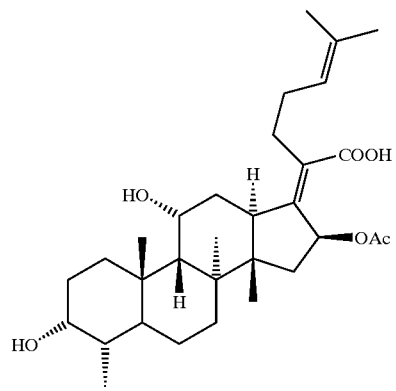

Fusidic acid

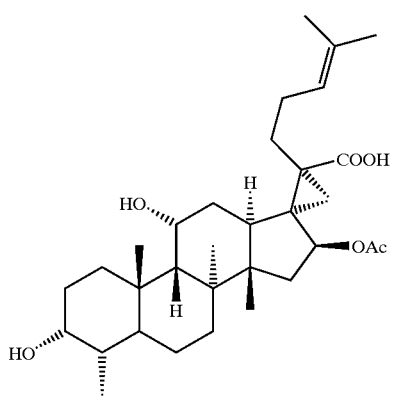

17(S),20(S)-Methanofusidic acid

TABLE 1

| Strain/identity | MIC value (concentration in µg/ml required for 90% inhibition) | | | | | |
|---|---|---|---|---|---|---|
| | Fusidic acid (1) | 101 | 102 | 104 | 107 | 110 |
| S. aureus ATC6538P | 0.125 | 0.125 | 0.125 | 0.125 | 0.25 | 0.125 |
| S. aureus ATCC 29213 | 0.125 | 0.125 | 0.25 | 0.125 | 1.0 | 0.125 |
| S. aureus CJ232* | 0.125 | 0.125 | 0.25 | 1.0 | 1.0 | 1.0 |
| S. aureus CJ234 (R)** | 0.004 | 0.004 | 0.25 | n.t. | n.t. | 0.004 |
| S. epidermidis ATCC12228 | 0.125 | 0.125 | 0.125 | 0.125 | 0.25 | 0.125 |
| Str. pyrogenes Leo id: EC5 | 4 | 16 | 64 | 64 | 64 | 64 |
| Str. pyrogenes NCTC8304 | 4 | 4 | 16 | 16 | 64 | 4 |
| Str.mitis Leo id: EG5 | 4 | 4 | 64 | 64 | 16 | 64 |
| Str. sp. ATCC12449 | 4 | 16 | 64 | 64 | 64 | 64 |
| Str. sp. Leo id: EF6 | 4 | 4 | 64 | 64 | 16 | 64 |
| Str. salvarius LEO-ID EG7 | 4 | 4 | 16 | 64 | 64 | 64 |
| Str. faecium*** Leo-id: E119(P) | 0.125 | 0.125 | 1 | 0.25 | 4 | 0.25 |

*MRSA;
**MRSA and Rifampicin resistant;
***penicillin resistant,
n.t. = not tested The following standard abbreviations are used throughout this disclosure:

AcOH = acetic acid
Ac₂O acetic anhydride
Ac = acetyl
Bu = n-butyl
ᵗBu, tBu = tert-butyl
Et = ethyl
Ether = diethyl ether
HF = hydrogen fluoride Me = methyl
MOM = methoxymethyl
MOMO = methoxymethyl-O
MRSA = meticilline resistant Staphylococcus aureus
Ph = phenyl
Piv = pivaloyl
TBAF = tetra-n-butylammonium fluoride
TBS = tert.butyl dimethylsilyl
TBSCl = tert.butyl dimethylsilyl chloride
THF = tetrahydrofuran
TLC = Thin Layer Chromatography
TMS = trimethylsilyl Preparations of Compounds of the Invention 17S,20S-Methanofusidic acid (9), may be prepared starting from naturally occurring fusidic acid by the sequence outlined in Scheme 1 below: Fusidic acid (1) is first converted into lactone (2) by deacetylation followed by acidification. The hydroxy group at C-3 is then protected with a TBS protective group by treating lactone (2) with TBSCl and imidazol in dry DMF yielding lactone (3). The double bond between C-17 and C-20 in (3) is selectively cyclopropanated with trimethylsulfoxoniumylide generated in situ from trimethylsulfoxonium iodide treated with NaH in dry DMF resulting attack solely from the α-face of the molecule yielding lactone (4). Reduction of the protected lactone (4) with LiAlH₄ yields diol (6) which is first protected selectively at the primary hydroxy group at C-21 with a diphenylmethylsilyl group followed by acetylation of the hydroxy group at C-16. After desilylation of (6) using tetrabutylammonium fluoride (TBA⁺F⁻) buffered with acetic acid, the free hydroxy group in (7) can be oxidised, first to the aldehyde by Dess-Martin periodinane and further to the carboxylic acid (8) by sodium chlorite. Compound (9) is obtained in a final step by cleavage of the TBS protective group in (8) by treating with aqueous hydrogen fluoride in THF.

The compound of formula 9 is a compound of the invention (Compound 101) and further a general starting compound for several analogues of formula I as hereinafter described.

Scheme 1

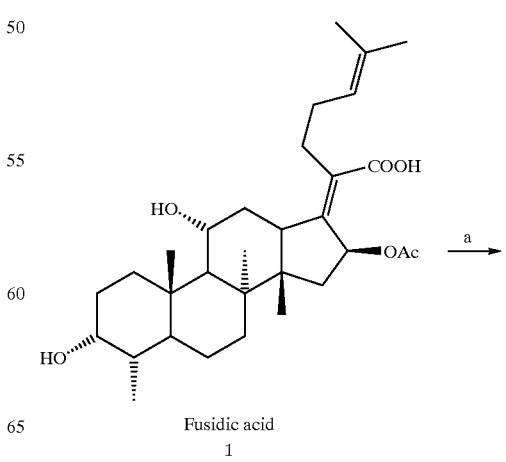

Fusidic acid
1

-continued
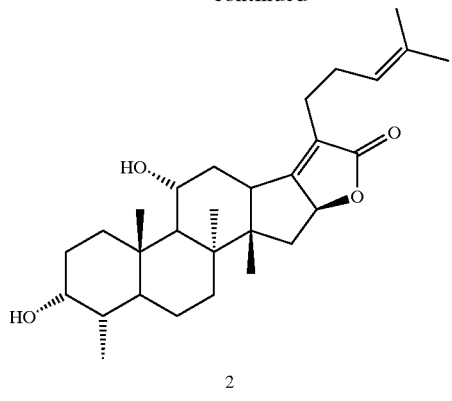
2
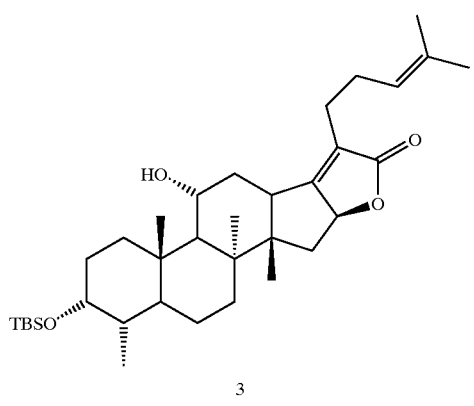
3
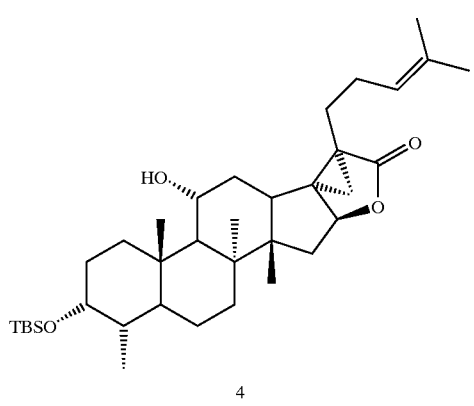
4
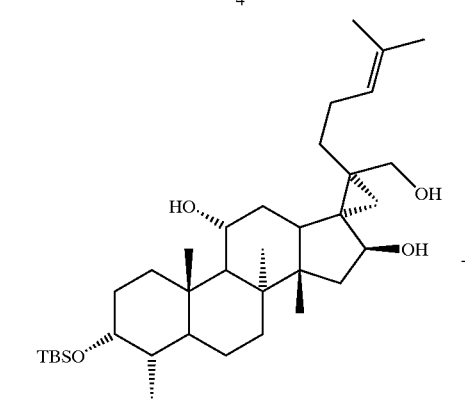
5
b →
c →
d →
e →
-continued
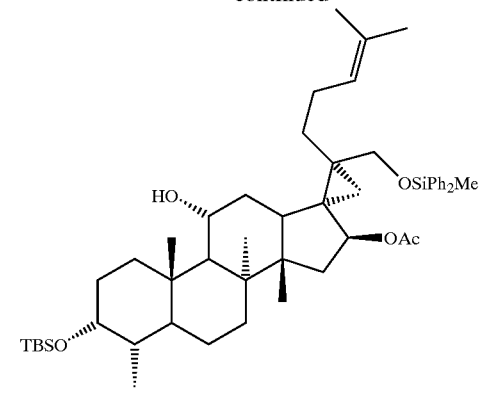
6
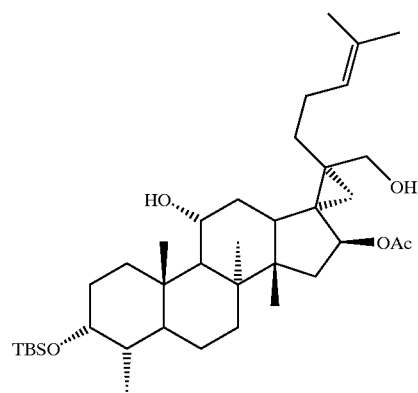
7
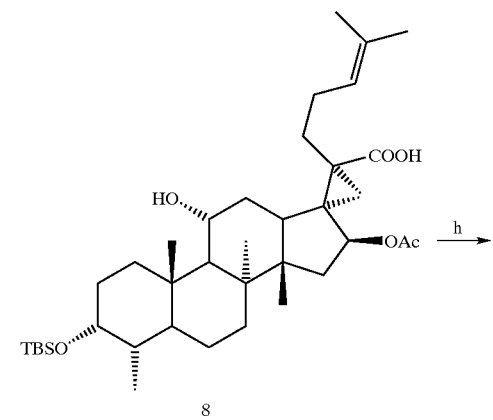
8
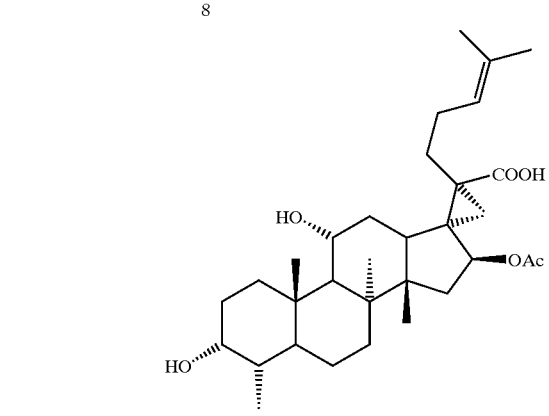
9
f →
g →
h →

Scheme 1. a) aq. NaOH in EtOH, reflux; ACOH; b) TBSCl, imidazol in DMF, r.t., overnight; c) trimethylsulfoxonium iodide, NaH in DMF, r.t., 6 h; d) LiAlH$_4$, THF, reflux; e); (i) Ph$_2$MeSiCl, Et$_3$N, CH$_2$Cl$_2$, −20° C. (ii) Ac$_2$O/pyridine; f) TBA$^+$F$^−$, AcOH, THF; g) (i) Dess-Martin periodinane, CH$_2$Cl$_2$/pyridine; (ii) NaClO$_2$, tert-BuOH; h) aq. HF in THF, r.t., 24 h.

The compounds of general formula I in which A represents an oxygen may be prepared by a method comprising a first step in which compounds of the general formula II are converted into 16-acyloxy or 16-O-alkyl compounds of formula III as described below:

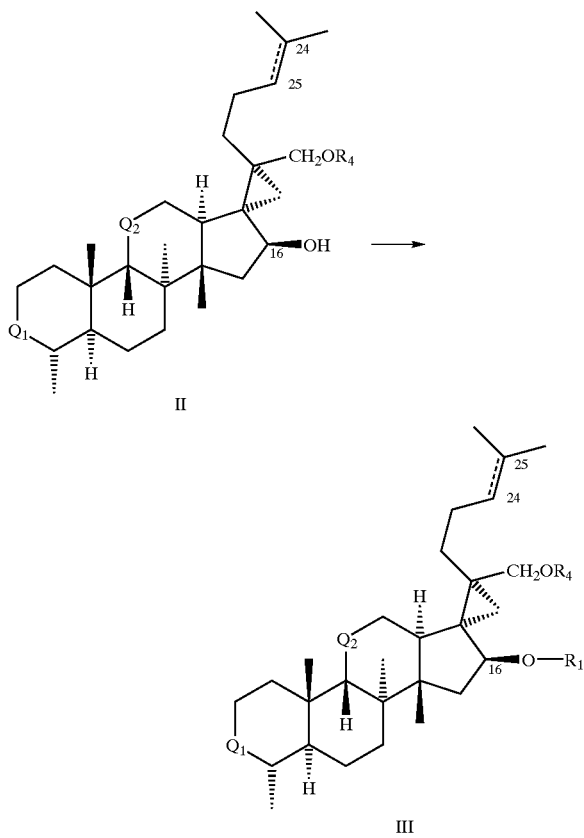

in which formulas $Q_1$, $Q_2$, $R_1$ and the dotted line between C-24 and C-25 have the meanings defined above; and R4 represents a common protective group such as alkanoyl, aralkanoyl, alkanoyloxyalkyl or aroyl, or a trisubstituted silyl radical substituted with alkyl, oxyalkyl, aryl or oxyaryl groups.

$R_4$ is preferably a silyl protective group such as diphenylmethylsilyl or tert.butoxydiphenylsilyl, or an acyl protective group such as acetyl or pivaloyl.

For compounds of formula III in which $R_1$ represents an alkyl radical as defined above, the conversion is performed by reacting a compound of formula II with an alkylhalide or an alkyltriflate according to general methods of ether preparations known to those skilled in the art. These compounds can for example be prepared as described below in Scheme 2 starting from diol (5) from Scheme 1.

For compounds of formula III in which $R_1$ represents an acyl group, the conversion is performed by reacting a compound of formula VI with an acylchloride or a corresponding acid anhydride in presence of a weak base according to general acylation methods known to those skilled in the art.

Compounds of formula III can be converted to compounds of formulas I by first removing the $R_4$ protective group by known methods and then by following the reaction steps h and i as outlined in Scheme 1 or by related methods known in the literature.

Diol (5) can be used as a general starting material for the preparation of compounds of the invention (Scheme 2). In a first step diol (5) is selectively protected at the primary hydroxy function by either an acid-labile protective group like the diphenylmethylsilyl group as in compound 10 or by a base-labile protective group like pivaloyl as in compound 11. These compounds can further be used for the preparation of compounds of the invention corresponding to formula 1 as described above for the transformation of compounds of formula II to compounds of formula III.

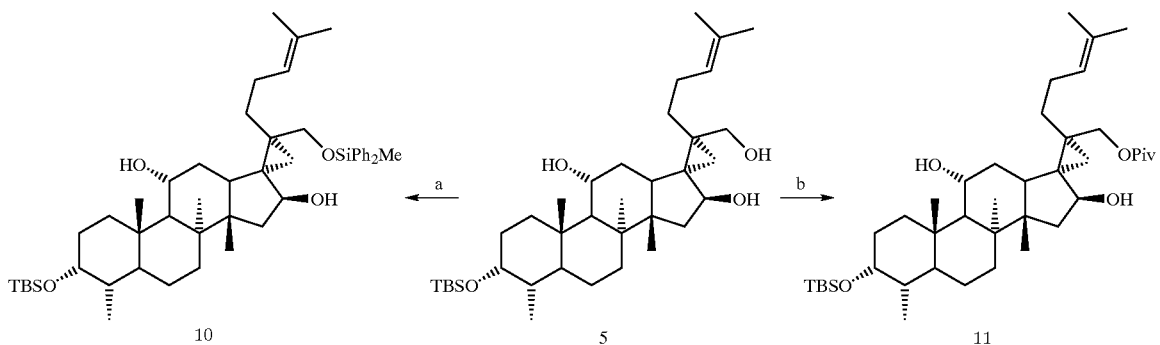

Scheme 2. a) Ph$_2$MeSiCl, Et$_3$N, CH$_2$Cl$_2$, −20° C., 3 h; b) Piv-Cl, pyridine, CH$_2$Cl$_2$, r.t., 3 h.

The compounds of formula I wherein Q$_1$ and/or Q$_2$ represent —(CO)— can also be prepared from the corresponding compounds of formula I wherein Q$_1$ and Q$_2$ both represent the group

by oxidation methods known by those skilled in the art.

The easily hydrolysable esters of the compounds of formula I and Ia can be prepared in known manner by methods described in the literature.

Compounds of the invention in which C-24 and C-25 are connected by a single bond can be prepared from the corresponding unsaturated analogues by reduction, e.g. by catalytic hydrogenation using catalysts such as palladium or platinum. Compounds such as helvolic acid and cephalosporin P$_1$ may be used as starting materials in the preparation of other compounds of general formula Ia.

Compounds of formula II are prepared starting from compounds in Scheme 1 by methods known from the literature (cf. GB Patent No. 1 490 852 and GB Patent No. 1 523 803) or by analogous methods. Starting compounds of formula III can for instance be prepared from the compound of formula 10 or more conveniently from the compound of formula 9 as outlined in Scheme 3.

It is a further object of the present invention to provide pharmaceutical compositions which are useful in the treatment of infectious diseases in the human and veterinary practice.

With this object in view, the composition of the invention contains as an active component at least one compound of formula I or Ia (hereinafter referred to as the active ingredient) including acceptable salts and easily hydrolysable esters thereof together with at least one pharmaceutically acceptable vehicle and/or diluent.

In said composition, the proportion of active ingredient to vehicle may vary from 0.5% to 100% by weight. The compositions can be worked up to various pharmaceutical forms of presentation such as granulates, tablets, pills, dragees, suppositories, capsules, sustained-release tablets, suspensions, injection and may be filled in bottles or tubes or similar containers. Pharmaceutical organic or inorganic, solid or liquid carriers and/or diluents suitable for oral, enteral, parenteral or topical administration can be used to make up compositions containing the present compounds: Water, gelatine, lactose, starch, magnesium stearate, talc, vegetable and animal oils and fats, benzyl alcohol, gum, polyalkylene glycol, petroleum jelly, cocoa butter, lanolin, and other emulsifying agents, salts for varying the osmotic pressure or buffers for securing an appropriate pH-value of the composition can be used as auxiliary agents.

Furthermore, the composition may contain other therapeutically active components which can appropriately be administered together with the compounds of the invention in the treatment of infectious diseases such as other suitable antibiotics, in particular such antibiotics which may enhance the activity and/or prevent development of resistance. Such antibiotics include penicillins, cephalosporins, tetracyclines, rifamycins, erythromycins, lincomycin, clindamycin and fluoroquinolones. Other compounds which advantageously may be combined with the compounds of the invention, especially in topical preparations, include e.g. corticosteroids, such as hydrocortisone or triamcinolone. Alternatively, such other therapeutically active component (s) may be administered concomitantly (either simultaneously or sequentially) with the composition of the invention.

For granulates, tablets, capsules or dragees the pharmaceutical composition of the invention appropriately contains from 25% to 98% of the active ingredient of the invention, and in oral suspensions the corresponding amount is appropriately from 2% to 20% active ingredient.

When the active ingredient is administered in the form of salts with pharmaceutically acceptable non-toxic bases. The preferred salts are for instance easily water-soluble or slightly soluble in water, in order to obtain a particular and appropriate rate of absorption.

As indicated above, the compounds of formula I and Ia and their salts may be included in pharmaceutical formulations, including suspensions, ointments and creams. A pharmaceutical preparation for oral administration may also be in form of a suspension of the active ingredient as such or in the form of a sparingly water-soluble pharmaceutically acceptable salt, the preparation containing from 20 to 100 mg per ml of vehicle. A pharmaceutical preparation for topical treatment may be in the form of an ointment or cream containing the active ingredient in an amount of from 0.5 to 50% of preparation. Topical preparations are favourable due to the stability towards sunlight and the relatively lipophilic nature of the present compounds.

Another object of the invention resides in the selection of a dose of the compounds of the invention which dose can be administered so that the desired activity is achieved without serious adverse effects. In the human systemic therapy the compounds and their salts are conveniently administered (to adults) in dosage units containing no less than 50 mg and up to 1000 mg, preferably from 200 to 750 mg, calculated as the compound of formula I.

By the term "dosage unit" is meant a unitary, i.e. a single dose which is capable of being administered to a patient, and which may be readily handled and packed, remaining as a physically and chemically stable unit dose comprising either the active ingredient alone or in admixture with one or more solid or liquid pharmaceutical diluents or vehicles.

In the form of a dosage unit, the compound may be administered one or more times a day at appropriate intervals, always depending, however, on the condition of the patient, and in accordance with the prescription made by the medical practitioner.

Thus in systemic treatment a daily dosage will preferably be an amount of from 0.5 to 3 g of the active ingredient.

The term "usage unit" in connection with topical use means a unitary, i.e. a single dose capable of being administered topically to a patient in an application per square centimeter of the infected area of from 0.1 mg to 10 mg and preferably from 0.2 mg to 1 mg of the active ingredient in question.

If the composition is to be injected, a sealed ampoule, a vial or a similar container may be provided containing a parenterally acceptable sterile aqueous or oily injectable solution or dispersion of the active ingredient as the dosage unit.

The parenteral preparations are in particular useful in the treatment of conditions in which a quick response to the treatment is desirable. In the continuous therapy of patients suffering from infectious diseases, the tablets or capsules may be the appropriate form of pharmaceutical preparation owing to the prolonged effect obtained when the drug is given orally, in particular in the form of sustained-release tablets.

In the treatment of infectious diseases, such tablets may advantageously contain other active components as mentioned above.

Still another object of the invention is to provide a method of treating patients suffering from infectious diseases, the method comprising administering to patients from 0.03 g to 0.7 g/kg body weight per day in 1 to 3 doses, preferably from 0.5 g to 3 g per day of a compound of formula I or Ia or an equivalent amount of a salt as defined before of a compound of formula I or Ia. Preferably, the active ingredient is given in the form of the dosage units as indicated above.

The invention will be further described in the following non-limiting Preparations and Examples.

PREPARATIONS AND EXAMPLES

General

All melting points are uncorrected. For $^{13}$C nuclear magnetic resonance (NMR) spectra (75.6 MHz) chemical shift values ($\delta$) (in ppm) are quoted, unless otherwise specified, for deuteriochloroform solutions relative to internal tetramethylsilane ($\delta$=0.00) or deuteriochloroform ($\delta$=76.81 for $^{13}$C NMR). Chromatography was performed on silica gel using ethyl acetate and low boiling petroleum ether as eluant. Anhydrous solvents were prepared by storing analytical grade solvents over 4 Å molecular sieves a few days prior to use.

Preparations

Preparation 1: 3-O-TBS-16-deacetyl-fusidic acid lactone (3)

16-Deacetyl-fusidic acid lactone (2) (2.0 g, 4.4 mmol) was dissolved in anhydrous DMF (10 ml). To the solution was added imidazole (0.6 mg, 8.8 mmol) and TBS-Cl (1.3 g, 8.8 mmol), and the reaction mixture was stirred overnight under an atmosphere of argon. After this time the reaction mixture was transferred to a separatory funnel with ethyl acetate (50 ml) and water (50 ml). The mixture was shaken and the two layers were separated. The aqueous layer was re-extracted with ethyl acetate and the combined organic layers were washed successively with water (30 ml) and brine (2×30 ml). The organic layer was dried over anhydrous sodium sulphate and concentrated under reduced pressure resulting a coiouriess solid. Recrystailusation from methanol yielded 2.4 g (96%) of 3 as a colourless powder, melting point 138.5–140° C.

$^{13}$C NMR, (CDCl$_3$): 176.4, 169.8, 132.5, 123.2, 123.1, 81.7, 71.6, 67.8, 55.0, 50.1, 40.6, 37.9, 37.1, 36.8, 35.8, 33.9, 32.3, 31.3, 30.6, 30.3, 27.2, 25.7, 25.5, 23.8, 23.2, 22.8, 20.3, 20.0, 17.9, 17.6, 16.6, –4.5, –5.1

Preparation 2: 3-OTBS-16-deacetyl-17S,20S-methanofusidic acid lactone (4)

In a dry Schlenck tube was placed a suspension of NaH in oil (60%, 270 mg, ca. 7.0 mmol). The NaH suspension was washed twice with pentane and evaporated to dryness under reduced pressure prior to the addition of anhydrous DMF (10 ml). Neat trimethylsulfoxonium iodide was added causing hydrogen formation. After stirring for 30 min at room temperature, a solution of lactone (3) (2.0 g, 3.5 mmol) in anhydrous DMF (10 ml) was added dropwise. The resulting reaction mixture was stirred for 6 hours at room temperature. After this time the reaction was quenched by poring the reaction mixture into 10% ice-cold aqueous HCl (100 ml) causing heavy precipitation of a white solid. The mixture was transferred to a separatory funnel with ether (150 ml). The two layers were shaken and separated. The aqueous layer was re-extracted with ether (100 ml) and the combined organic layers were washed successively with water (50 ml) and brine (2×50 ml). The organic layer was dried over anhydrous sodium sulphate and concentrated under reduced pressure resulting a colourless solid. Recrystallisation from methanol yielded 1.9 g (96%) of 3 as a colourless powder.

$^{13}$C NMR, (CDCl$_3$): 178.2, 132.1, 123.7, 84.5, 71.6, 68.0, 50.4, 50.0, 44.1, 40.3, 38.3, 37.1, 36.6, 36.4, 36.0, 33.1, 32.8, 30.7, 30.5, 30.3, 30.2, 25.7, 25.6, 25.5, 23.6, 22.7, 20.4, 18.1, 17.9, 17.6, 17.5, 16.5, –4.6, –5.1

Preparation 3: 3-O-TBS-16β-hydroxy-17S,20S-methanofusidin-3,11,16,21-tetrol (5)

Lithium aluminium hydride (0.4 g, 100 mmol) was suspended in anhydrous THF (30 ml) under argon in a an oven-dried two-necked round bottom flask fitted with a condenser. To the stirred suspension was added a solution of lactone (4) (1.75 g, 3.0 mmol) in anhydrous THF (10 ml) in such a rate causing gentle reflux. The reaction mixture was refluxed under vigorous stirring for 3 hours and then allowed to attain room temperature. Excess lithium aluminium hydride was destroyed with ethyl acetate (50 ml), and water (50 ml) was then added slowly. The resulting suspension was acidified with diluted hydrochloric acid to pH 5. The suspension was transferred to a separatory funnel with ethyl acetate (50 ml) and water. (30 ml). The two layers were shaken well and separated. The aqueous layer was re-extracted with ethyl acetate (50 ml) and the combined organic layers were washed twice with brine (2×30 ml). The organic layer was dried over anhydrous sodium sulphate and concentrated under reduced pressure yielding 1.76 g of essentially pure title compound diol (5) as a colourless white powder. An analytically pure sample was obtained by recrystallisation from hot methanol, melting point 155–164° C.

$^{13}$C NMR, (CDCl$_3$): 131.0, 124.6, 79.8, 71.8, 68.5, 67.7, 48.8, 48.7, 44.5, 44.3, 39.6, 38.1, 37.0, 36.2, 36.2, 36.0, 34.5, 33.4, 30.7, 30.4, 25.7, 25.5, 25.3, 24.5, 22.0, 22.0, 20.2, 18.1, 17.9, 17.5, 16.6, –4.6, –5.1

Preparation 4: 3-O-TBS-21-O-diphenylmethylsilyl-16β-acetoxy-17S,20S-methanofusidin-3,11,16,21-tetrol (6)

A. Diol (5) (1.5 g, 2.5 mmol) was dissolved in anhydrous dichloromethane (20 ml) and triethylamine (0.7 ml, 5 mmol) under argon in a an oven-dried two-necked round bottom flask and cooled at –25° C. To the cooled solution was added over a period of 15 min a solution of diphenylmethylchlorosilane (0.57 ml, 2.75 mmol) in anhydrous dichloromethane (5 ml) so that the temperature did not exceed –20° C. and stirring was continued for 15 min. The reaction mixture was transferred to a separatory funnel and diluted with 30 ml dichloromethane. The organic solution was washed successively with saturated sodium bicarbonate (30 ml), water (30 ml) and brine (30 ml). The organic solution was dried over anhydrous sodium sulphate and solvents were evaporated under reduced pressure yielding 1.96 g (quantitative) of a colourless syrup of 3-O-TBS-21-O-diphenylmethylsilyl-16β-hydroxy-17S,20S-methanofusidin-3,11,16,21-tetrol (6).

$^{13}$C NMR, (CDCl$_3$): 135.1, 135.0, 134.1, 130.9, 129.8, 127.8, 127.7, 124.3, 78.8, 71.8, 68.6, 67.4, 49.4, 48.2, 43.3, 43.0, 39.7, 38.4, 37.0, 36.5, 36.0, 34.8, 34.5, 33.0, 30.7, 30.6, 30.3, 25.7, 25.5, 25.2, 24.1, 22.4, 20.4, 19.5, 18.5, 17.9, 17.4, 16.6, –3.4, –4.6, –5.1

B. The crude mixture was without purification acetylated by dissolving in pyridine (10 ml) and acetic anhydride (5 ml). The resulting mixture was stirred overnight at room temperature in a stoppered bottle. After this time the reaction mixture was concentrated under reduced pressure yielding a pale yellow oil. Essentially pure title compound (6), 1.85 g (90%), was obtained as a colourless syrup after column chromatography using a mixture of ethyl acetate and low boiling petroleum ether as eluent.

Preparation 5: 3-O-TBS-16β-acetoxy-17S,20S-methanofusidin-3,11,16,21-tetrol (7)

3-O-TBS-21-O-diphenylmethylsilyl-16β-acetoxy-17S, 20S-methanofusidin-3,11,16,21-tetrol (6) (1.9 g, 2.3 mmol) was dissolved in tetrahydrofuran (30 ml) and glacial acetic acid (0.25 ml). To this solution was added tetrabutyl ammonium fluoride hydrate (1.17 g, 4.6 mmol) and the reaction mixture was stirred at room temperature for 15 min. The reaction mixture was then transferred to a separatory funnel with 100 ml ethyl acetate. The organic solution was washed twice with water (2×25 ml) and brine (25 ml). The organic layer was dried over anhydrous sodium sulphate and concentrated under reduced pressure yielding a colourless syrup. Pure title compound (7), 1.3 g (90%), was obtained as a colourless syrup after column chromatography using a mixture of ethyl acetate and low boiling petroleum ether as eluant.

$^{13}$C NMR, (CDCl$_3$): 169.9, 136.0, 136.0, 134.2, 130.7, 129.5, 127.6, 124.6, 82.7, 71.8, 68.5, 67.5, 48.9, 48.8, 44.5, 40.9, 39.7, 37.0, 36.3, 36.0, 35.5, 34.5, 33.4, 33.2, 30.7, 30.4, 29.2, 25.7, 25.6, 25.3, 25.1, 24.2, 22.1, 21.0, 20.2, 17.9, 17.8, 17.6, 16.6, 14.0, −3.2, −4.6, −5.1

Preparation 6: 3-O-TBS-17S,20S-methanofusidic acid (8)

A. Neat Dess-Martin periodinane (0.89 g, 2.1 mmol) was added portionwice to a solution of 3-O-TBS-16β-acetoxy-17S,20S-methanofusidin-3,11,16,21-tetrol (7) (1.26 g, 2.0 mmol) in anhydrous THF (20 ml) under argon at 0° C. The reaction mixture was stirred for 3 hours. After this time 1N sodium bicarbonate (50 ml) and 1N 1N sodium thiosulfate (50 ml) were added to the reaction mixture and the two layers were vigorously stirred for 30 min. The two layers were transferred to a separatory funnel with ethyl acetate (100 ml). The two layers were separated and the organic layer was washed with saturated sodium bicarbonate (100 ml) and brine (100 ml). The organic layer was dried over anhydrous sodium sulphate and concentrated under reduced pressure yielding 1.25 g of a colourless syrup.

$^{13}$C NMR, (CDCl$_3$): 169.7, 131.2, 124.3, 83.4, 71.8, 68.3, 67.2, 48.7, 44.4, 41.5, 39.6, 37.1, 36.1, 35.4, 34.5, 33.4, 30.7, 30.4, 30.0, 25.7, 25.5, 25.1, 24.4, 22.9, 22.0, 21.3, 20.2, 17.9, 17.7, 17.5, 16.6, −4.6, −5.1

B. Crude 3-O-TBS-16β-acetoxy-17S,20S-methanofusidin-21-al-3,11,16-triol (1.25 g, 2.0 mmol) from A was without purification dissolved in tert.butanol (15 ml). To this solution was added 2-methyl-2-butene (0.48 ml, 5.4 mmol), 1N sodium dihydrogenphosphate (5.5) and sodium chlorite (0.46 g, 5.0 mmol) in water (20 ml) and the resulting reaction mixture was stirred vigorously overnight at room temperature. The reaction mixture was acidified to pH 4 with acetic acid and transferred to a separatory funnel with ethyl acetate (50 ml). The two layers were shaken and separated. The aqueous layer was re-extracted twice with ethyl acetate (2×30 ml). The combined organic extracts were washed twice with brine (2×20 ml), dried over anhydrous sodium sulphate and concentrated under reduced pressure yielding 1.2 g of a pale yellow foam. Purification by column chromatography using a mixture of ethyl acetate, low boiling petroleum ether and a trace of formic acid as eluant yielded 1.05 g (81% from 7) of pure acid 8, the title compound, as a semi-crystalline compound.

$^{13}$C NMR, (CDCl$_3$): 200.0, 169.7, 131.8, 123.7, 79.5, 71.7, 68.1, 48.9, 48.4, 44.4, 43.3, 40.9, 40.8, 39.6, 37.1, 36.2, 36.1, 33.7, 33.3, 30.6, 30.4, 26.8, 26.0, 25.7, 25.5, 24.4, 23.4, 22.1, 20.6, 20.1, 17.9, 17.5, 16.5, −4.6, −5.1

Preparation 7: 3-O-TBS-21-O-diphenylmethylsilyl-17S,20S-methanofusidin-3,11,16,21-tetrol (10)

3-O-TBS-16β-hydroxy-17S,20S-methanofusidin-3,11,16,21-tetrol (5) (1.5 g, 2.5 mmol) was dissolved in anhydrous dichloromethane (20 ml) and triethylamine (0.7 ml, 5 mmol) under argon in a an oven-dried two-necked round bottom flask and cooled at −25° C. To the cooled solution was added over a period of 15 min a solution of diphenylmethylchlorosilane (0.57 ml, 2.75 mmol) in anhydrous dichloromethane (5 ml) so that the temperature did not exceed −20° C. and stirring was continued for 15 min. The reaction mixture was transferred to a separatory funnel and diluted with 30 ml dichloromethane. The organic solution was washed successively with saturated sodium bicarbonate (30 ml), water (30 ml) and brine (30 ml). The organic solution was dried over anhydrous sodium sulphate and solvents were evaporated under reduced pressure yielding 1.96 g (quantitative) of a colourless syrup. Pure title compound (10), 1.8 g (91%), was obtained as a colourless syrup after column chromatography using a mixture of ethyl acetate and low boiling petroleum ether as eluent.

$^{13}$C NMR, (CDCl$_3$): 179.4, 169.8, 131.9, 123.5, 79.5, 71.7, 68.3, 49.0, 48.7, 48.5, 48.3, 44.0, 42.2, 40.5, 39.6, 37.0, 36.3, 36.2, 36.0, 34.2, 33.2, 30.6, 30.5, 30.4, 26.0, 25.7, 25.4, 24.3, 22.1, 21.1, 20.2, 20.1, 17.9, 17.6, 17.4, 16.6, −4.6, −5.1

Preparation 8: 3-O-TBS-21-O-Piv-17S,20S-methanofusidin-3,11,16,21-tetrol (11)

Diol (5) (1 g, 1.7 mmol) was dissolved in anhydrous dichloromethan (5 ml) and anhydrous pyridine (1.5 ml) and cooled at 0° C. Piv-Cl (0.25 ml, 1.95 mmol) was added dropwice and the reaction mixture was stirred for 3 hours at 0° C. The reaction mixture was diluted with ethyl acetate (100 ml), transferred to a separatory funnel and washed successively with water (2×20 ml) and brine (2×20 ml). The organic solution was dried over anhydrous sodium sulphate and solvents were evaporated under reduced pressure yielding 1.1 g (98%) of the title compound (11) as a colourless oil which crystallised upon standing for a few hours.

$^{13}$C NMR, (CDCl$_3$): 178.2, 131.3, 124.1, 79.1, 71.8, 68.5, 67.8, 49.5, 48.2, 43.4, 42.3, 39.7, 38.7, 38.0, 37.0, 36.6, 35.9, 34.4, 32.9, 32.2, 31.5, 30.6, 30.3, 27.1, 25.7, 25.5, 25.0, 23.9, 22.4, 20.4, 19.1, 19.0, 17.9, 17.4, 16.6, −4.6, −5.1

EXAMPLES

Example 1

17S,20S-Methanofusidic acid (Compound 101)

3-O-TBS-17S,20S-methanofusidic acid (8) (1.0 g, 1.55 mmol) was dissolved in THF (12 ml) in a round bottom teflon flask and 40% aqueous HF (3 ml) and the resulting mixture was stirred vigorously at room temperature for 24 hours. After this time the pH of the reaction mixture was adjusted to ca. 5 with 2N NaOH. The mixture was transferred to a separatory funnel with ethyl acetate (30 ml) and water (20 ml), shaken well and the two layers were separated. The aqueous layer was re-extracted with ethyl acetate (3×30 ml) and the combined organic layers were washed with brine (3×15 ml). The organic solution was dried over anhydrous sodium sulphate and concentrated under reduced pressure yielding 1.4 g of compound 101 as a colourless solid. Recrystallisation from methanol-water yielded 0.82 g of colourless crystals, melting point 243–245° C.

$^{13}$C NMR, (CD$_3$OD), 176.9, 172.3, 132.7, 125.2, 81.1, 72.5, 68.6, 50.8, 45.2, 41.8, 41.0, 39.8, 38.1, 37.9, 37.0, 36.5, 33.1, 32.6, 31.1, 31.0, 27.3, 25.9, 24.2, 23.7, 22.4, 21.5, 20.5, 18.0, 17.7, 16.5

Example 2

24,25-Dihydro-17S,20S-methanofusidic acid
(Compound 102)

A solution of compound 101 (280 mg, 0.53 mmol) in ethanol (3 ml) was hydrogenated under 1 atmosphere of hydrogen in the presence of 5% palladium on calcium carbonate (30 mg). The reaction mixture was stirred vigorously until the theoretical amount of hydrogen was consumed and the catalyst was removed by filtration. Water was added dropwise to the filtrate yielding 255 mg crystalline 24,25-dihydro-17S,20S-methanofusidic acid (Compound 102), melting point 138.5–140° C.

$^{13}$C NMR, (CD$_3$OD): 177.3, 172.4, 81.0, 72.5, 68.7, 50.9, 45.1, 41.8, 41.0, 40.3, 39.5, 38.6, 38.1, 37.9, 37.0, 36.5, 33.1, 32.7, 31.1, 31.0, 29.1, 26.6, 24.2, 23.7, 23.1, 23.0, 22.4, 21.3, 20.5, 18.0, 16.5

Example 3

11-Dehydro-17S,20S-methanofusidic acid
(Compound 103)

A. 3-O-TBS-11-Dehydro-17S,20S-methanofusidic acid

To a solution of 3-O-TBS-17S,20S-methanofusidic acid (200 mg, 0.3 mmol) dissolved in acetic acid (2.5 ml) was added a solution of chromic acid (65 mg, 0.65 mmol) in water (0.65 ml), and the resulting green reaction mixture was stirred for 3 hours at room temperature. The reaction mixture was diluted with diethyl ether (40 ml), washed with water (20 ml) and twice with brine (2×10 ml), dried over anhydrous sodium sulphate and concentrated under reduced pressure yielding 180 mg of 3-O-TBS-11-dehydro-17S,20S-methanofusidic acid as a colourless oil.

B. 11-Dehydro-17S,20S-methanofusidic acid

3-O-TBS-11-dehydro-17S,20S-methanofusidic acid (180 mg, 0.28 mg) from A was dissolved in THF (2 ml) in a round bottom plastic vial and 40% aqueous HF (0.5 ml) and the resulting mixture was stirred vigorously at room temperature for 24 hours. After this time the pH of the reaction mixture was adjusted to ca. 5 with 2N NaOH. The mixture was transferred to a separatory funnel with ethyl acetate (20 ml) and water (20 ml), shaken well and the two layers were separated. The aqueous layer was re-extracted with ethyl acetate (3×20 ml) and the combined organic layers were washed with brine (3×15 ml). The organic solution was dried over anhydrous sodium sulphate and concentrated under reduced pressure yielding 1.4 g of compound 101 as colourless semi-crystalline product of 11-dehydro-17S,20S-methanofusidic acid were obtained from methanol-water, melting point 136–149° C.

$^{13}$C NMR, (CD$_3$OD): 213.2, 176.3, 172.0, 132.9, 125.0, 81.1, 72.3, 59.6, 50.7, 50.2, 45.9, 43.9, 40.9, 39.1, 38.9, 38.7, 38.2, 36.7, 33.6, 33.1, 31.1, 30.1, 27.3, 25.9, 22.8, 22.2, 22.1, 21.9, 20.4, 17.7, 16.6

Example 4

3-Dehydro-17S,20S-methanofusidic acid
(Compound 104)

17S,20S-Methanofusidic acid (260 mg, 0.5 mmol) was dissolved in tetrahydrofuran (10 ml) and cooled at 0° C. Solid Dess-Martin periodinane (250 mg, 0.59 mmol) was added in small portions and the reaction was stirred for 5 hours. The reaction mixture was diluted with ethyl acetate (40 ml) and transferred to a separatory funnel. The organic solution was shaken vigorously with 10% aqueous sodium thiosulphate (15 ml), washed with water (10 ml) and brine (10 ml). The organic layer was dried over anhydrous sodium sulphate and concentrated under reduced pressure affording a colourless syrup. Purification by column chromatography using mixtures of petroleum ether-ethyl acetate-formic acid as eluant yielded 215 mg of 3-dehydro-17S,20S-methanofusidic acid.

Example 5

16-Deacetoxy-16β-propionyloxy-17S,20S-methanofusidic acid (Compound 105)

A. 3-O-TBS-21-O-diphenylmethylsilyl-16β-propionyloxy-17S,20S-fusidin-3,11,16,21-tetrol Compound of formula 10 (400 mg, 0.51 mmol) was dissolved in anhydrous dichloromethan (5 ml) and anhydrous pyridine (1 ml) in a dry Schlenck tube and cooled at 0° C. Propionyl chloride (0.06 ml, 0.68 mmol) was added dropwice to the cooled solution via a syringe and the resulting reaction mixture was stirred under argon for 5 hours at room temperature. The reaction mixture was transferred to a separatory funnel with ethyl acetate (30 ml) and water (20 ml). The mixture was shaken and the two layers were separated. The aqueous layer was re-extracted with ethyl acetate (30 ml) and the combined organic layers were washed with water (20 ml) and brine (20 ml). The organic solution was dried over anhydrous sodium sulphate and concentrated under reduced pressure affording a colourless syrup. Pure compound 380 mg (88%), was obtained as a colourless syrup after column chromatography using a mixture of ethyl acetate and low boiling petroleum ether as eluent.

$^{13}$C NMR, (CDCl$_3$): 173.0, 136.0, 134.1, 130.7, 129.5, 127.6, 124.6, 82.6, 71.8, 68.5, 67.6, 48.9, 48.8, 44.6, 41.0, 39.7, 37.0, 36.3, 36.0, 35.6, 34.6, 33.4, 33.2, 30.7, 30.4, 29.1, 27.7, 25.7, 25.6, 25.5, 25.3, 24.2, 22.1, 20.2, 17.9, 17.6, 16.6, 8.6, −3.2, −4.6, −5.1

B. 3-O-TBS-16β-propionyloxy-17S,20S-methanofusidin-3,11,16,21-tetrol

3-O-TBS-21-d iphenylmethylsilyl-16β-propionyloxy-17S,20S-methanofusidin-3,11,16,21-tetrol (370 mg, 0.44 mmol) from A was dissolved in tetrahydrofuran (6 ml) and glacial acetic acid (0.05 ml). To this solution was added tetrabutyl ammonium fluoride hydrate (220 mg, 088 mmol) and the reaction mixture was stirred at room temperature for 20 min. The reaction mixture was then transferred to a separatory funnel with 25 ml ethyl acetate. The organic solution was washed twice with water (2×10 ml) and brine (10 ml). The organic layer was dried over anhydrous sodium sulphate and concentrated under reduced pressure yielding a colourless syrup. Pure title compound, 260 mg (92%) was obtained as a colourless syrup after column chromatography using a mixture of ethyl acetate and low boiling petroleum ether as eluant.

C. 3-O-TBS-16β-propionyloxy-17S,20S-methanofusidic acid

Neat Dess-Martin periodinane (0.89 g, 2.1 mmol) was added portionwise to a solution of 3-O-TBS-16β-propionyloxy-17S,20S-methanofusidin-3,11,16,21-tetrol (250 mg, 0.39 mmol) from B in anhydrous THF (4 ml) under argon at 0° C. The reaction mixture was stirred for 3 hours. After this time 1N sodium bicarbonate (10 ml) and 1N 1N sodium thiosulfate (10 ml) were poured into the reaction mixture and the two layers were vigorously stirred for 30 min. The two layers were transferred to a separatory funnel with ethyl acetate (40 ml). The two layers were separated and the organic layer was washed with saturated sodium bicarbonate (20 ml) and brine (40 ml). The organic layer was dried over anhydrous sodium sulphate and concentrated under reduced pressure yielding 250 mg of a colourless syrup.

$^{13}$C NMR, (CDCl$_3$): 200.0, 173.0, 131.8, 123.8, 79.3, 71.7, 68.2, 48.9, 48.4, 44.4, 43.3, 40.9, 40.8, 39.6, 37.1, 36.2, 36.1, 33.7, 33.3, 30.6, 30.4, 27.3, 26.8, 25.9, 25.7, 25.5, 24.4, 23.6, 22.1, 20.1, 17.9, 17.5, 17.5, 16.5, 8.5, −4.6, −5.1

The crude aldehyde (250 mg, 0.39 mmol) was without purification dissolved in tert-butanol (3 ml). To this solution was added 2-methyl-2-butene (0.1 ml, 1 mmol), 1N sodium dihydrogenphosphate (1.1 ml) and sodium chlorite (100 mg, 1.0 mmol) in water (4 ml) and the resulting reaction mixture was stirred vigorously overnight at room temperature. The reaction mixture was acidified to pH 4 with acetic acid and transferred to a separatory funnel with ethyl acetate (20 ml). The two layers were shaken and separated. The aqueous layer was re-extracted twice with ethyl acetate (2×20 ml). The combined organic extracts were washed twice with brine (2×15 ml), dried over anhydrous sodium sulphate and concentrated under reduced pressure yielding 250 mg of a pale yellow foam. Purification by column chromatography using a mixture of ethyl acetate, low boiling petroleum ether and a trace of formic acid as eluant yielded 205 mg (79%) of pure acid, the title compound, as a semi-crystalline compound.

$^{13}$C NMR, (CDCl$_3$): 179.2, 173.1, 131.9, 123.5, 79.3, 71.7, 68.3, 49.0, 48.5, 44.1, 40.6, 39.8, 39.6, 37.0, 36.3, 36.2, 36.0, 34.3, 33.2, 30.6, 30.6, 30.4, 26.7, 26.1, 25.7, 25.5, 24.4, 22.2, 21.4, 20.2, 17.9, 17.7, 17.4, 16.6, 8.6, −4.6, −5.1

D. 16-Deacetoxy-16β-propionyloxy-17S,20S-methanofusidic acid

3-O-TBS-16β-propionyloxy-17S,20S-methanofusidic acid (190 mg, 0.29 mmol) from C was dissolved in THF (3 ml) in a round bottom teflon flask and 40% aqueous HF (1 ml) and the resulting mixture was stirred vigorously at room temperature for 24 hours. After this time the pH of the reaction mixture was adjusted to ca. 5 with 2N NaOH. The mixture was transferred to a separatory funnel with ethyl acetate (15 ml) and water (10 ml), shaken well and the two layers were separated. The aqueous layer was re-extracted with ethyl acetate (3×15 ml) and the combined organic layers were washed with brine (3×10 ml). The organic solution was dried over anhydrous sodium sulphate and concentrated under reduced pressure yielding 120 mg (76%) of compound 105 as a colourless solid. Recrystallisation from methanol-water yielded 100 mg of colourless powder.

$^{13}$C NMR, (CDCl$_3$): 178.8, 173.3, 132.1, 123.8, 79.4, 71.4, 68.3, 49.3, 48.6, 44.2, 40.8, 39.9, 39.8, 37.1, 36.4, 36.3, 36.1, 34.8, 32.6, 30.9, 30.4, 30.0, 26.9, 26.3, 25.7, 24.5, 22.6, 21.4, 20.8, 17.7, 17.6, 15.9, 8.9

Example 6–9

16-Deacetoxy-16β-acyloxy-17S,20S-methanofusidic acids (Compounds 106–110)

A. 16β-Acyloxy derivatives of 3-O-TBS-21-O-diphenylmethylsilyl-17S,20S-methanofusidin-3,11,16,21-tetrol By following the procedure given in Example 5 A and substituting the acyl chlorides listed in Table 2 for the propionyl chloride, the 16β-acyloxy of 3-O-TBS-21-O-diphenylmethysilyl-16β-hydroxy-17S,20S-methanofusidin-3,11,16,21-tetrol indicated in Table 2 were prepared.

TABLE 2

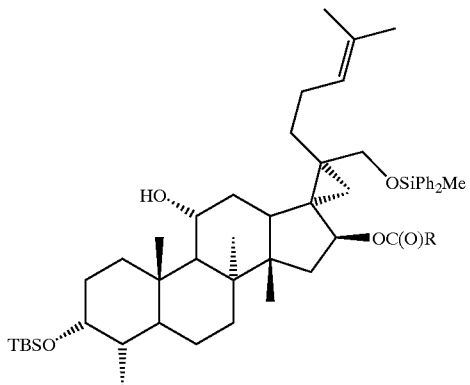

IV

| Example | Acyl chloride | Resulting compound, R |
|---------|---------------|------------------------|
| 6A | Cyclohexylcarbonyl chloride | $C_6H_{11}$ |
| 7A | Isopropionyl chloride | $CH(CH_3)_2$ |
| 8A | 4-Fluorobenzoyl chloride | $C_6H_4F$ |
| 9A | Furfuryl chloride | $C_4H_4O$ |

$^{13}$C NMR of Compound 106A, (CDCl$_3$): 174.6, 136.1, 136.0, 134.1, 134.1, 130.7, 129.5, 127.6, 124.7, 82.5, 71.8, 68.5, 67.6, 48.9, 48.8, 44.7, 43.2, 41.2, 39.7, 37.0, 36.3, 36.0, 35.9, 34.6, 33.4, 33.2, 30.7, 30.4, 29.0, 28.7, 28.2, 25.9, 25.7, 25.5, 25.5, 25.4, 25.4, 25.1, 24.2, 22.1, 20.2, 18.1, 17.9, 17.6, 16.6, −3.3, −4.6, −5.1

$^{13}$C NMR of Compound 107A, (CDCl$_3$): 175.5, 136.0, 134.1, 130.7, 129.5, 127.6, 124.6, 82.7, 71.8, 68.5, 67.7, 48.9, 48.8, 44.7, 41.1, 39.7, 37.0, 36.3, 36.0, 35.9, 34.6, 34.0, 33.4, 33.1, 30.7, 30.4, 29.0, 25.9, 25.7, 25.5, 25.3, 24.2, 22.1, 20.2, 18.6, 18.1, 18.0, 17.9, 17.6, 16.6, −3.3, −4.6, −5.1

$^{13}$C NMR of Compound 108A, (CDCl$_3$): 165.3, 164.2, 135.7, 135.6, 134.0, 131.6, 130.9, 129.4, 127.4, 126.8, 124.5, 115.4, 115.1, 83.4, 71.8, 68.5, 67.2, 48.9, 48.9, 44.9, 41.2, 39.7, 37.1, 36.2, 36.1, 35.6, 34.7, 33.5, 33.3, 30.7, 30.4, 29.1, 25.7, 25.5, 25.4, 25.3, 24.4, 22.0, 20.2, 18.3, 17.9, 17.6, 16.6, −3.6, −4.6, −5.1

³C NMR of Compound 109A, (CDCl₃): 157.5, 145.9, 145.0, 135.9, 135.8, 134.1, 130.8, 129.4, 127.4, 124.6, 116.9, 111.5, 83.5, 71.8, 68.5, 67.2, 48.9, 48.8, 44.8, 41.0, 39.7, 37.1, 36.2, 36.1, 35.7, 34.5, 33.4, 33.3, 30.7, 30.4, 29.2, 25.7, 25.5, 25.3, 25.1, 24.3, 22.1, 20.2, 17.9, 17.6, 16.6, −3.6, −4.6, −5.1

B. 16β-Acyloxy derivatives of 3-O-TBS-17S,20S-methanofusidin-3,11,16,21-tetrol By following the procedure of Example 5B and replacing 3-O-TBS-21-O-diphenylmethylsilyl-16β-propionyloxy-17S,20S-methanofusidin-3,11,16,21-tetrol with the 16β-acyloxy derivatives of 3-O-TBS-21-O-diphenylmethylsilyl-17S,20S-methanofusidin-3,11,16,21-tetrol listed in Table 2, the 16β-acyloxy derivatives of 3-O-TBS-17S,20S-methanofusidin-3,11,16,21-tetrol shown in Table 3 were prepared.

TABLE 3

V

| Example | Resulting compound, R |
|---|---|
| 6B | C₆H₁₁ |
| 7B | CH(CH₃)₂ |
| 8B | C₆H₄F |
| 9B | C₄H₄O |

C. 3-OTBS-16β-acyloxy-17S,20S-methanofusidic acid

By following the procedure of Example 5C and replacing 3-O-TBS-21-O-16β-propionyloxy-17S,20S-methanofusidin-3,11,16,21-tetrol with the 16β-acyloxy derivatives of 3-O-TBS-17S,20S-methanofusidin-3,11,16,21-tetrol listed in Table 3, the 16β-acyloxy derivatives of 3-O-TBS-17S,20S-methanofusidic acid shown in Table 4 were prepared.

TABLE 4

V

| Example | Resulting compound, R |
|---|---|
| 6C | C₆H₁₁ |
| 7C | CH(CH₃)₂ |
| 8C | C₆H₄F |
| 9C | C₄H₄O |

¹³C NMR of Compound 106C, (CDCl₃): 178.8, 174.7, 131.8, 123.6, 79.1, 71.7, 68.3, 49.0, 48.5, 44.2, 41.9, 40.7, 39.7, 39.6, 37.0, 36.3, 36.1, 36.0, 34.2, 33.2, 30.6, 30.4, 29.1, 27.8, 26.2, 25.7, 25.6, 25.5, 25.5, 24.8, 24.3, 22.2, 21.8, 20.6, 20.2, 17.9, 17.8, 17.4, 16.6, −4.6, −5.1

¹³C NMR of Compound 107C, (CDC₁₃): 179.2, 175.7, 131.8, 123.6, 79.3, 71.7, 68.3, 49.0, 48.5, 44.2, 40.7, 39.8, 39.6, 37.0, 36.3, 36.2, 36.0, 34.3, 33.2, 32.8, 30.6, 30.5, 30.4, 26.1, 25.7, 25.5, 24.3, 22.2, 21.7, 20.5, 20.2, 19.0, 17.9, 17.8, 17.4, 16.6, −4.6, −5.1

¹³C NMR of Compound 108C, (CDCl₃): 177.6, 165.4, 164.1, 134.1, 133.7, 132.1, 131.7, 129.7, 127.7, 126.1, 123.6, 115.1, 80.6, 71.7, 68.2, 48.8, 48.7, 44.9, 41.0, 40.1, 39.6, 37.1, 36.2, 36.1, 36.0, 34.2, 33.4, 30.7, 26.2, 25.7, 25.5, 24.6, 23.1, 21.9, 20.1, 18.0, 17.9, 17.4, 16.6, −4.6, −5.1

¹³C NMR of Compound 109C, (CDCl₃): 177.7, 157.3, 146.1, 144.4, 131.7, 123.7, 117.6, 111.5, 80.4, 71.7, 68.3, 48.8, 48.6, 44.7, 40.8, 40.0, 39.6, 37.1, 36.2, 36.1, 34.2, 33.4, 30.7, 30.5, 30.2, 26.3, 25.7, 25.5, 24.5, 22.7, 22.0, 20.1, 17.9, 17.7, 17.5, 16.6, −4.6, −5.1

D. 16β-Acyloxy-17S,20S-methanofusidic acid

By following the procedure of Example 5D and replacing 3-O-TBS-16β-propionyloxy-17S,20S-methanofusidic acid replacing with derivatives of 3-O-TBS-16β-acyloxy-17S,20S-methanofusidic acid listed in Table 4, the 16β-acyloxy derivatives of 17S,20S-methanofusidic acid shown in Table 5 were prepared.

TABLE 4

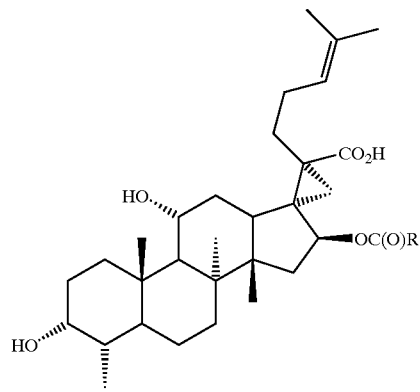

V

| Example | Resulting compound, R | Compound |
|---|---|---|
| 6D | $C_6H_{11}$ | 106 |
| 7D | $CH(CH_3)_2$ | 107 |
| 8D | $C_6H_4F$ | 108 |
| 9D | $C_4H_4O$ | 109 |

$^{13}$C NMR of Compound 106, (CDCl$_3$): 177.4, 165.6, 164.3, 132.3, 131.8, 126.3, 123.9, 115.3, 80.8, 71.4, 68.3, 49.1, 48.8, 45.0, 41.1, 40.2, 39.8, 37.2, 36.3, 36.1, 35.9, 34.6, 32.7, 30.4, 30.4, 29.9, 26.4, 25.7, 24.6, 23.3, 22.4, 20.7, 18.0, 17.6, 15.9

$^{13}$C NMR of Compound 107, (CDCl$_3$): 179.0, 175.8, 132.0, 123.8, 79.4, 71.4, 68.3, 49.3, 48.6, 44.4, 40.9, 40.0, 39.8, 37.1, 36.4, 36.2, 34.7, 33.1, 32.5, 30.8, 30.3, 29.9, 26.3, 25.7, 24.4, 22.7, 21.9, 20.8, 19.2, 18.1, 17.8, 17.6, 15.9

$^{13}$C NMR of Compound 108, (CDCl$_3$): 177.4, 165.6, 164.3, 132.3, 131.8, 126.3, 123.9, 115.3, 80.8, 71.4, 68.3, 49.1, 48.8, 45.0, 41.1, 40.2, 39.8, 37.2, 36.3, 36.1, 35.9, 34.6, 32.7, 30.4, 30.4, 29.9, 26.4, 25.7, 24.6, 23.3, 22.4, 20.7, 18.0, 17.6, 15.9

$^{13}$C NMR of Compound 109, (CDCl$_3$): 176.7, 159.1, 148.2, 146.0, 132.7, 125.3, 119.7, 113.0, 82.2, 72.5, 68.6, 50.7, 50.0, 45.7, 42.1, 41.1, 40.2, 38.2, 38.0, 38.0, 37.1, 36.6, 33.2, 32.3, 31.1, 27.5, 25.9, 24.3, 23.5, 22.7, 22.3, 18.2, 17.7, 16.5

Example 10

16-Deacetoxy-16β-ethoxy-17S,20S-methanofusidic acid (Compound 110)

A. 3-O-TBS-21-O-Piv-16β-ethoxy-17S,20S-methanofusidin-3,11,16,21-tetrol

3-O-TBS-21-O-Piv-17S,20S-methanofusidin-3,11,16,21-tetrol (11) (400 mg, 0.6 mmol) was dissolved in anhydrous dichloromethan (4 ml) in a dry Schlenck tube. To this solution was added successively 2,6-di-tert.butyl pyridine and (0.4 ml, 1.8 mmol) and ethyl trifluoromethansulfonate (0.2 ml, 1.52 mmol) and the resulting mixture was stirred at room temperature for 24 hours. After this time the reaction mixture was concentrated under reduced pressure and purified by column chromatography using a mixture of ethyl acetate and low boiling petroleum ether as eluant yielding 340 mg (81%) of 3-O-TBS-21-O-Piv-16β-ethoxy-17S,20S-methanofusidin-3,11,16,21-tetrol as a semi-crystalline compound.

$^{13}$C NMR (CDCl$_3$): 178.6, 130.9, 124.5, 86.7, 71.8, 68.9, 68.7, 64.4, 49.3, 48.6, 42.5, 39.8, 38.7, 37.8, 37.0, 36.8, 36.6, 35.9, 33.9, 33.0, 32.2, 30.9, 30.6, 30.4, 27.1, 25.7, 25.5, 25.1, 24.0, 22.4, 21.8, 20.5, 18.0, 17.9, 17.5, 16.6, 15.3, –4.6, –5.1

B. 3-O-TBS-16β-ethoxy-17S,20S-methanofusidin-3,11,16,21-tetrol

To a suspension of lithium aluminium hydride (55 mg, 1.4 mmol) in anhydrous THF (10 ml) was added a solution of 3-O-TBS-21-O-Piv-16β-ethoxy-17S,20S-methanofusidin-3,11,16,21-tetrol (330 mg, 0.47 mmol) from A in anhydrous THF (3 ml) under cooling with an ice-bath. The reaction mixture was stirred vigorously at room temperature for 3 hours. Excess litium aluminium hydride was destroyed by adding ethyl acetate. Water was added to the suspension and the mixture was then acidified with aqueous HCl to pH 4. The mixture was transferred to a separatory funnel with ethyl acetate (30 ml) and water (20 ml). The two layers were shaken and separated. The aqueous layer was re-extracted with ethyl acetate (30 ml) and the combined organic layers were washed with water (20 ml) and brine (20 ml), dried over anhydrous sodium sulfate and concentrated to yield 260 mg (90%) essentially pure 3-O-TBS-16β-ethoxy-17S,20S-methanofusidin-3,11,16,21-tetrol which crystallised slowly upon standing.

$^{13}$C NMR (CDCl$_3$): 130.8, 124.7, 88.2, 71.8, 68.5, 67.7, 64.4, 48.8, 48.7, 44.0, 39.6, 38.1, 37.2, 37.0, 36.6, 36.2, 36.2, 34.7, 33.5, 30.7, 30.6, 30.4, 25.7, 25.5, 25.3, 24.5, 23.0, 22.0, 20.3, 17.9, 17.5, 16.6, 14.8, –4.6, –5.1

C. 3-O-TBS-16β-ethoxy-17S,20S-methanofusidic acid

Neat Dess-Martin periodinane (182 mg, 0.43 mmol) was added portionwise to a solution of 3-O-TBS-16β-ethoxy-17S,20S-methanofusidin-3,11,16,21-tetrol (230 mg , 0.39 mmol) from B in anhydrous THF (4 ml) under argon at 0° C. The reaction mixture was stirred for 3 hours. After this time 1N sodium bicarbonate (10 ml) and 1N 1N sodium thiosulfate (10 ml) were added to the reaction mixture and the two layers were vigorously stirred vigorously for 30 min. The two layers were transferred to a separatory funnel with ethyl acetate (40 ml). The two layers were separated and the organic layer was washed with saturated sodium bicarbonate (20 ml) and brine (40 ml). The organic layer was dried over anhydrous sodium sulphate and concentrated under reduced pressure yielding 220 mg of a colourless syrup.

$^{13}$C NMR, (CDCl$_3$): 200.0, 131.5, 124.2, 84.4, 71.8, 68.4, 64.4, 49.0, 48.6, 44.0, 43.3, 42.9, 39.7, 37.5, 37.0, 36.3, 36.1, 33.7, 33.3, 30.7, 30.4, 27.5, 26.1, 25.7, 25.5, 24.4, 22.5, 22.2, 20.3, 17.9, 17.5, 17.4, 16.6, 14.6, –4.6, –5.1

The crude aldehyde (220 mg, 0.36 mmol) was without purification dissolved in tert.butanol (3 ml). To this solution was added 2-methyl-2-butene (0.1 ml, 1 mmol), 1N sodium dihydrogenphosphate (1.1 ml) and sodium chlorite (100 mg, 1.0 mmol) in water (4 ml) and the resulting reaction mixture was stirred vigorously overnight at room temperature. The reaction mixture was acidified to pH 4 with acetic acid and transferred to a separatory funnel with ethyl acetate (20 ml). The two layers were shaken and separated. The aqueous layer was re-extracted twice with ethyl acetate (2×20 ml). The combined organic extracts were washed twice with brine (2×15 ml), dried over anhydrous sodium sulphate and concentrated under reduced pressure yielding 250 mg of a pale yellow foam. Purification by column chromatography using a mixture of ethyl acetate, low boiling petroleum ether and a trace of formic acid as eluant yielded 175 mg (71%) of pure acid, the title compound, as a semi-crystalline compound.

$^{13}$C NMR, (CDCl$_3$): 178.8, 131.5, 124.0, 84.4, 71.8, 68.5, 64.7, 49.0, 48.7, 43.4, 41.7, 39.7, 37.9, 37.0, 36.3, 36.1, 34.3, 33.3, 30.7, 30.4, 26.0, 25.7, 25.5, 24.4, 22.2, 20.9, 20.3, 17.9, 17.6, 17.4, 16.6, 14.6, −4.5, −5.1

D. 16-Deacetoxy-16β-ethoxy-17S,20S-methanofusidic acid

3-O-TBS-16β-ethoxy-17S,20S-methanofusidic acid (150 mg, 0.24 mmol) from C was dissolved in THF (3 ml) in a round bottom plastic vial and 40% aqueous HF (1 ml) and the resulting mixture was stirred vigorously at room temperature for 24 hours. After this time the pH of the reaction mixture was adjusted to ca. 5 with 2N NaOH. The mixture was transferred to a separatory funnel with ethyl acetate (15 ml) and water (10 ml), shaken well and the two layers were separated. The aqueous layer was re-extracted with ethyl acetate (3×15 ml) and the combined organic layers were washed with brine (3×10 ml). The organic solution was dried over anhydrous sodium sulphate and concentrated under reduced pressure yielding 95 mg (76%) of compound 110 as a colourless solid. iu Recrystailisation from methanol-water yielded 75 mg of colourless powder, melting point 142–146° C.

$^{13}$C NMR, (CDCl$_3$): 177.6, 132.4, 125.4, 86.3, 72.5, 68.8, 66.3, 51.0, 50.0, 44.3, 42.0, 41.1, 39.4, 38.2, 38.1, 37.9, 36.9, 36.5, 33.2, 33.1, 31.0, 27.3, 25.9, 24.1, 23.8, 22.5, 21.0, 18.0, 17.7, 16.5, 15.1

Example 11

16-Deacetoxy-16β-(1',1',1'-trifluoroethoxy)-17S, 20S-methanofusidic acid (Compound 111)

A. 3-O-TBS-21-O-Piv-16β-(1',1',1'-trifluoroethoxy)-17S,20S-methanofusidin-3,11,16,21-tetrol By following the procedure given in Example 10A and substituting ethyl trifluoromethansulfonate for 1,1,1-trifluoroethyl trifluoromethansulfonate, 3-O-TBS-21-O-Piv-16β-(1',1',1'-trifluoroethoxy)-17S,20S-methanofusidin-3,11,16,21-tetrol was prepared.

B. 3-O-TBS-16β-(1',1',1'-trifluoroethoxy)-17S,20S-methanofusidin-3,11,16,21-tetrol By following the procedure of Example 10B and replacing 3-O-TBS-21-O-Piv-16β-ethoxy-17S,20S-methanofusidin-3,11,16,21-tetrol with 3-O-TBS-21-O-Piv-16β-(1',1',1'-trifluoroethoxy)-17S,20S-methanofusidin-3,11,16,21-tetrol from 11A, 3-O-TBS-16β-(1',1',1'-trifluoroethoxy)-17S,20S-methanofusidin-3,11,16,21-tetrol was prepared.

C. 3-O-TBS-16β-(1',1',1'-trifluoroethoxy)-17S,20S-methanofusidic acid

By following the procedure of Example 10C and replacing 3-O-TBS-16β-ethoxy-17S,20S-methanofusidin-3,11,16, 21-tetrol with 3-O-TBS-16β-(1',1',1'-trifluoroethoxy)-17S, 20S-methanofusidin-3,11,16,21-tetrol from 11C, 3-O-TBS-16β-(1',1',1'-trifluoroethoxy)-17S,20S-methanofusidic acid was prepared.

D. 16-Deacetoxy-16β-(1',1',1'-trifluoroethoxy)-17S, 20S-methanofusidic acid By following the procedure of Example 10D and replacing 3-O-TBS-16β-ethoxy-17S,20S-methanofusidic acid replacing with 3-O-TBS-16β-(1',1',1'-trifluoroethoxy)-17S, 20S-methanofusidic acid from 11C, 16-Deacetoxy-16β-(1', 1',1'-trifluoroethoxy)-17S,20S-methanofusidic acid was prepared.

Example 12

16-Deacetoxy-16β-methoxymethyl-17S,20S-methanofusidic acid (Compound 112)

A. 3-O-TBS-21-O-Piv-16β-methoxymethyl-17S, 20S-methanofusidin-3,11,16,21-tetrol 3-O-TBS-21-O-Piv-17S,20S-methanofusidin-3,11,16,21-tetrol (11) (400 mg, 0.59 mmol) was dissolved in anhydrous dichloromethan (4 ml) in a dry Schlenck tube and cooled at 0° C. To this solution was added successively diisopropylethylamine (0.3 ml, 1.8 mmol) and MOM-Cl (0.1 ml, 1.4 mmol) and the resulting mixture was stirred 0° C. for 24 hours. After this time the reaction mixture was concentrated under reduced pressure and purified by column chromatography using a mixture of ethyl acetate and low boiling petroleum ether as eluant yielding 330 mg (78%) of 3-O-TBS-21-O-Piv-16β-methoxymethyl-17S,20S-methanofusidin-3,11,16,21-tetrol as a semi-crystalline solid.

B. 3-O-TBS-16β-methoxymethyl-17S,20S-methanofusidin-3,11,16,21-tetrol

By following the procedure of Example 10B and replacing 3-O-TBS-21-O-Piv-16β-ethoxy-17S,20S-methanofusidin-3,11,16,21-tetrol with 3-O-TBS-21-O-Piv-16β-methoxymethyl-17S,20S-methanofusidin-3,11,16,21-tetrol from 12A, 3-O-TBS-16β-methoxymethyl-17S,20S-methanofusidin-3,11,16,21-tetrol was prepared.

$^{13}$C NMR, (CDCl$_3$): 130.9, 124.6, 96.3, 86.8, 71.8, 68.5, 67.5, 56.5, 48.9, 48.6, 43.8, 39.6, 39.5, 37.0, 36.9, 36.5, 36.3, 36.1, 34.7, 33.3, 30.7, 30.4, 25.7, 25.6, 25.4, 24.4, 22.4, 22.1, 20.3, 17.9, 17.5, 17.4, 16.6, −4.6, −5.1

C. 3-O-TBS-16β-methoxymethyl-17S,20S-methanofusidic acid

By following the procedure of Example 10C and replacing 3-O-TBS-16β-ethoxy-17S,20S-methanofusidin-3,11,16, 21-tetrol with 3-O-TBS-16β-methoxymethyl-17S,20S-methanofusidin-3,11,16,21-tetrol from 12C, 3-O-TBS-16β-methoxymethyl-17S,20S-methanofusidic acid was prepared.

$^{13}$C NMR, (CDCl$_3$): 179.1, 131.7, 123.7, 97.7, 84.2, 71.7, 68.4, 55.5, 49.4, 48.5, 42.2, 40.6, 40.0, 39.6, 36.9, 36.6, 36.3, 35.9, 34.1, 32.9, 31.9, 30.6, 30.3, 25.9, 25.7, 25.5, 24.0, 22.5, 20.4, 18.7, 17.9, 17.4, 16.6, −4.6, −5.1

D. 16-Deacetoxy-16β-methoxymethyl-17S,20S-methanofusidic acid

By following the procedure of Example 10D and replacing 3-O-TBS-16β-ethoxy-17S,20S-methanofusidic acid replacing with 3-O-TBS-16β-methoxymethyl-17S,20S-methanofusidic acid from 11C, 16-deacetoxy-16β-methoxymethyl-17S,20S-methanofusidic acid was prepared, melting point 130–134° C.

$^{13}$C NMR, (CDCl$_3$): 178.9, 132.0, 123.9, 97.7, 84.2, 71.4, 68.5, 55.7, 49.8, 48.7, 42.2, 40.7, 40.2, 39.8, 37.1, 36.5, 36.4, 36.2, 34.6, 32.4, 32.2, 30.3, 30.0, 26.1, 25.7, 24.1, 22.9, 21.0, 18.8, 17.6, 17.5, 15.9

Example 13

3-Dehydro-3β-bromo-17S,20S-methanofusidic acid (Compound 113)

A. 17S,20S-Methanofusidic acid, pivaloyl ester 17S,20S-Methanofusidic acid (400 mg, 0.76 mmol) was dissolved in anhydrous dimethylformamide (5 ml). Triethylamine (1.1 ml, 7.6 mmol) and chloromethylpivalate (1.1 ml, 7.6 mmol) were added successively to the stirred solution and the resulting reaction mixture was stirred under argon at room temperature for 24 hours. After this time the reaction mixture was transferred to a separatory funnel with ethyl acetate (80 ml) and washed with water (3×40 ml) and brine (2×40 ml) The organic solution was dried over anhydrous sodium sulfate and concentrated under reduced pressure yielding 705 mg of a pale yellow oil. Pure compound was obtained after column chromatography using a mixture of ethyl acetate and low boiling petroleum ether as eluant yielding 320 mg (66%) of 17S,20S-methanofusidic acid, pivaloyl ester as a colourless solid.

$^{13}$C NMR, (CDCl$_3$): 176.1, 170.8, 169.1, 131.3, 123.4, 79.3, 77.8, 69.1, 65.7, 49.0, 47.9, 42.1, 39.2, 38.2, 38.1, 36.3, 36.3, 35.6, 35.0, 34.8, 31.6, 31.0, 30.1, 29.4, 26.4, 25.4, 25.3, 23.3, 22.8, 20.8, 20.3, 18.2, 17.5, 17.3, 16.2

B. 3-Dehydro-3β-bromo-17S,20S-methanofusidic acid, pivaloyl ester 17S,20S-Methanofusidic acid, pivaloyl ester (210 mg, 0.34 mmol) from A was dissolved in anhydrous benzene (5 ml). Triphenylphosphine (270 mg, 1 mmol) and tetrabromomethan (450 mg, 1.3 mmol) were added successively to the stirred solution and the resulting reaction mixture was stirred under argon at room temperature for 24 hours. After this time ether (20 ml) was added and the white precipitate of triphenylphosphine was removed by filtration. The etheral solution was concentrated under reduced pressure to a yellow oil and purified by column chromatography using a mixture of ethyl acetate and low boiling petroleum ether as eluant yielding 190 mg (79%) of 3-dehydro-3β-bromo-17S, 20S-methanofusidic acid, pivaloyl ester as a colourless solid.

$^{13}$C NMR, (CDCl$_3$): 177.1, 171.3, 169.9, 132.2, 123.5, 79.7, 78.4, 68.2, 62.6, 49.6, 48.5, 45.4, 42.3, 41.5, 40.1, 39.8, 38.8, 38.3, 37.2, 36.8, 36.3, 35.1, 35.0, 32.4, 32.0, 26.9, 25.9, 25.7, 24.0, 23.8, 22.2, 20.7, 18.9, 18.5, 17.8, 17.6

C. 3-Dehydro-3β-bromo-17S,20S-methanofusidic acid

3-Dehydro-3β-bromo-17S,20S-methanofusidic acid, pivaloyl ester (180 mg, 0.25 mmol) from B was dissolved in methanol (3 ml) and cooled at 0° C. To the cooled solution was added an aqueous solution potassium carbonate (90 mg, 0.66 mmol) and the resulting reaction mixture was stirred for 6 hours. After this time water (3 ml) was added and the solution was acidified with 4 N hydrochloric acid to pH 3. The mixture was transferred to a separatory funnel with ether (20 ml). Water (10 ml) was added, the resulting mixture was shaken and the two layers were separated. The aqueous layer was re-extracted with ether (2×15 ml) and the combined organic layers were washed with brine. The organic layer was dried over anhydrous sodium sulfate and concentrated to an oil. Pure compound was obtained by column chromatography using a mixture of ethyl acetate, low boiling petroleum ether and a trace of formic acid as eluant yielding 120 mg (79%) of 3-dehydro-3β-bromo-17S, 20S-methanofusidic acid as a colourless powder, melting point 180–181° C.

$^{13}$C NMR, (CDCl$_3$): 179.1, 169.9, 132.2, 123.6, 79.4, 68.2, 62.6, 49.2, 48.6, 45.6, 43.9, 41.2, 40.7, 39.7, 39.6, 37.3, 36.9, 36.4, 35.2, 35.1, 32.8, 31.0, 26.2, 25.7, 24.2, 23.7, 22.1, 21.1, 20.4, 18.9, 17.6, 17.5

Example 14

3-Dehydro-3β-chloro-17S,20S-methanofusidic acid (Compound 114)

A. 3-Dehydro-3β-chloro-17S,20S-methanofusidic acid, pivaloyl ester

By following the procedure of Example 13B and replacing tetrabromomethan with tetrachloromethan, 3-dehydro-3β-chloro-17S,20S-methanofusidic acid, pivaloyl ester was prepared.

B. 3-Dehydro-3β-chloro-17S,20S-methanofusidic acid

By following the procedure of Example 13C and replacing 3-dehydro-3β-bromo-17S,20S-methanofusidic acid, pivaloyl ester with 3-dehydro-3β-chloro-17S,20S-methanofusidic acid, pivaloyl ester from 13C, 3-dehydro-3β-chloro-17S,20S-methanofusidic acid was prepared.

Example 15

Cream

| | |
|---|---|
| 24,25-Dihydro-17S,20S-methanofusidic acid, sodium salt | 1 g |
| Petrolatum | 7.5 g |
| Liquid paraffin | 7.5 g |
| Spermaceti | 2.5 g |
| Sorbitane monopalmitate | 2.5 g |
| Polyoxyethylene sorbitane monopalmitate | 2.5 g |
| Water | 26.5 g |
| | 50 g |

Heat petrolatum, paraffin, spermaceti, sorbitane monopalmitate and polyoxyethylene sorbitane monopalmitate to 70° C. and slowly add water under continuous stirring. Continue stirring until the cream has cooled. Triturate 24,25-dihydro-17S,20S-methanofusidic acid, sodium salt into the cream base and homogenise using a roller mill. Fill the cream into aluminium collapsible tubes.

Example 16

Ointment

| | |
|---|---|
| 16-Deacetoxy-16β-ethoxy-17S,20S-methanofusidic acid, sodium salt | 1 g |
| Liquid paraffin | 6.9 g |
| Cetanol | 0.2 g |
| Lanolin anhydrous | 2.3 g |
| Petrolatum | 39.6 g |
| | 50 g |

Melt paraffin, cetanol, lanolin and petrolatum at 70° C. After cooling to below 40° C. triturate 16-deacetoxy-16β-ethoxy-17S,20S-methanofusidic acid, sodium salt. Fill the ointment into lacquered collapsible aluminium tubes.

Example 17

Capsules

| | |
|---|---|
| 16-Deacetoxy-16β-propionyloxy-17S,20S-methanofusidic acid, sodium salt | 25 g |
| Microcrystalline cellulose | 14.5 g |
| Magnesium stearate | 0.5 g |
| | 40 g |

Pass the ingredients through a 60 mesh sieve and mix for 10 min. Fill the mixture into hard gelatine capsules using a capsule fill weight of 400 mg.

Example 18

Tablets

| | |
|---|---|
| 16-Deacetoxy-16β-(2',2',2'-trifluoroethoxy)-17S,20S-methanofusidic acid, sodium salt | 25 g |
| Avicel ™ | 12 g |
| STA-Rx 1500 | 12 g |
| Magnesium stearate | 1 g |
| | 50 g |

16-Deacetoxy-16β-(2',2',2'-trifluoroethoxy)-17S,20S-methanofusidic acid, sodium salt, Avicel™ and STA-Rx are mixed together, sieved through a 0.7 mm sieve and thereafter mixed with magnesium stearate: The mixture is pressed into tablets each of 500 mg.

Example 19

Suspension

| | |
|---|---|
| 16-Deacetoxy-16β-ethoxy-17S,20S-methanofusidic acid, sodium salt | 1 g |
| Citric acid | 0.09 g |
| Sodium monohydrogenphosphate | 0.14 g |
| Sucrose | 5 g |
| Tween ™ 80 | 0.01 g |
| Potassium sorbate | 0.04 g |
| Carboxymethylcellulose-Na | 0.1 g |
| Water | qs. to 100 ml suspension. |

The crystals are micronized and suspended in a solution of citric acid, sodium monohydrogen phosphate, sucrose, potassium sorbate and Tween™ 80 in 10 ml water, if necessary with slight warming. Carboxymethylcellulose-Na is dissolved in 4 ml boiling water. After cooling, it is added to the other ingredients. The suspension is homogenised in a blender and finally water is added to a total volume of 100 ml.

Example 20

Ointment

| | |
|---|---|
| A: A: 16-Deacetoxy-16β-(2',2',2',-trifluoroethoxy)-17S,20S-methanofusidic acid, sodium salt | 1 g |
| B: One of the compounds: hydrocortisone, triamcinolone or fluocinolone | 0.5 g |
| Liquid paraffin | 6.9 g |
| Cetanol | 0.2 g |
| Lanolin anhydrous | 2.3 g |
| Petrolatum | 39.1 g |
| | 50 g |

Melt paraffin, cetanol, lanolin and petrolatum at 70° C. After cooling to below 40° C., triturate A and B. Fill the ointment into lacquered collapsible aluminium tubes.

Example 21

Ointment

| | |
|---|---|
| A: 17S,20S-Methanofusidic acid, sodium salt | 1.5 g |
| B: Tetracycline | 1.5 g |
| Liquid paraffin | 13.8 g |
| Cetanol | 0.4 g |
| Lanolin anhydrous | 4.6 g |
| Petrolatum | 78.2 g |
| | 100 g |

Melt paraffin, cetanol, lanolin and petrolatum at 70° C. After cooling to below 40° C., triturate A and B. Fill the ointment into lacquered collapsible aluminium tubes.

Example 22

Eye Gel

| | |
|---|---|
| 17S,20S-Methanofusidic acid, sodium salt | 10 g |
| Benzalkonium chloride | 0.1 g |
| Carbomer | 5 g |
| Mannitol | 50 g |
| Sodium edetate | 0.5 g |
| Sodium hydroxide | q.s. |
| Sterile water | up to 100 g |

Dissolve disodium edetate and mannitol in water for injection in a stainless steel vessel equipped with a stirring tool and a built-in homogenizer. Add Carbomer 934P, evacuate the vessel and autoclave the dispersion under slow stirring and homogenizing at high speed. Cool down to 70° C., stop agitator and homogenizer. Add 17S,20S-Methanofusidic acid, sodium salt micronized, sterile—evacuate the vessel and let the 17S,20S-Methanofusidic acid, sodium salt sink during slow agitation. Homogenize at high speed for 10 minutes at 70° C. Cool down to below 30° C. during stirring and homogenizing at low speed. Add a sterile solution of benzalkonium chloride in water for injection under slow stirring. Neutralise the carbomer 934 P by adding a sterile solution of sodium hydroxide 1.050 kg in water for injection. Stir and homogenize at low speed for 5 minutes. Adjust—if necessary—the pH to 5.4–5.8. Transfer the eye gel to storage tanks using nitrogen pressure and the low speed homogenizing transfer system. Store at room temperature until filling. The eye gel is filled aseptically in sterile tubes using a fill weight of 3.5 g.

What is claimed is:

1. A compound of the general formula I

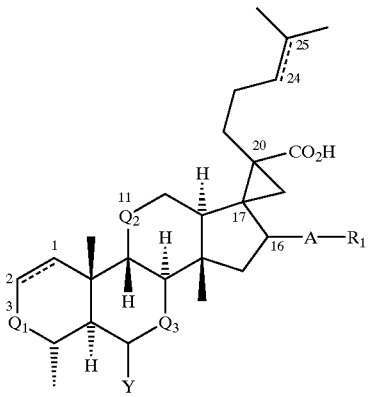

wherein
- $Q_1$, $Q_2$ and $Q_3$ are the same or different and independently represent a —(CO)— group; a —(CHOH)— group; a —(CHOR)— group; a —(CHSH)— group; a —(CHNH$_2$)— group; a —(C═X)— group, wherein X represents halogen; or a —(CHNHR)— group, wherein R represents an alkyl radical having 1 to 4 carbon atoms or an acyl radical having 1 to 4 carbon atoms; and wherein $Q_2$ and $Q_3$ may also independently represent a —(CH$_2$)— group;
- Y represents hydrogen, hydroxy, an alkyl radical having 1 to 4 carbon atoms, or an acyl radical having 1 to 4 carbon atoms; A represents an oxygen or sulphur atom;
- $R_1$ represents an alkyl radical having 1 to 4 carbon atoms, an olefinic group having 2 to 4 carbon atoms, a ($C_1$–$C_6$) acyl group, a ($C_3$–$C_7$)cycloalkylcarbonyl group or a benzoyl group, $R_1$ being optionally substituted with one or more halogen atoms and/or hydroxy, alkoxy or azido groups;

and pharmaceutically acceptable salts and easily hydrolysable esters thereof.

2. A compound according to claim 1 and having the general formula Ia

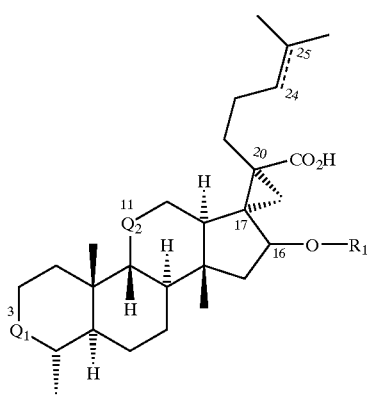

wherein
- $Q_1$ and $Q_2$ are the same or different and independently represent a —(CHOH)— group; a —(CO)— group, or a —(CHSH)— group; or wherein $Q_1$ is a —(C═X)— group, wherein X is halogen;
- $R_1$ represents an alkyl radical having 1 to 4 carbon atoms, an olefinic group having 2 to 4 carbon atoms, a ($C_1$–$C_6$) acyl group, ($C_1$–$C_7$)cycloalkylcarbonyl group or a benzoyl group, $R_1$ optionally being substituted with one or more halogen atoms and/or hydroxy, alkoxy or azido groups;

and pharmaceutically acceptable salts and easily hydrolysable esters thereof.

3. A compound according to claim 1 or 2 wherein Q1 and Q2 is selected from the group consisting of —(CO)— and —(CHOH)—.

4. A compound according to claim 1 or 2 wherein $Q_1$ and $Q_2$ both represent a

group.

5. A compound according to claim 1 or 2 wherein one of $Q_1$ or $Q_2$ represents —(CO)—.

6. A compound according to claim 1, wherein A represents oxygen.

7. A compound according to claim 1 or 2 wherein $R_1$ represents a ($C_1$–$C_4$)alkyl group, optionally substituted with one or more substituents selected from the group consisting of azido, hydroxy, and halogen selected from fluoro, chloro and bromo.

8. A compound according to claim 7 wherein $R_1$ represents a ($C_1$–$C_4$)alkyl group substituted with one or more halogen groups selected from fluoro and chloro.

9. A compound according to claim 1 wherein $R_1$ is selected from the group consisting of ethyl, 2,2,2-trifluoroethyl, 2,2,2-trichloroethyl, 2-azidoethyl, 2-hydroxyethyl, propyl, tert-butyl, isopropyl, 1,3-difluoro-isopropyl, tert-butyl, acetyl, propionyl, chloroacetyl and trifluoroacetyl.

10. A compound according to claim 1 or 2, wherein $R_1$ is ($C_1$–$C_4$)acyl or benzoyl, optionally substituted by one or more halogen atoms.

11. A compound according to claim 1 wherein the bond between C-24 and C-25 is a double bond.

12. A compound of formula I selected from the group consisting of 17S,20S-Methanofusidic acid, Compound 101
24,25-Dihydro-17S,20S-methanofusidic acid, Compound 102
11-Dehydro-17S,20S-methanofusidic acid, Compound 103
3-dehydro-17S,20S-methanofusidic acid, Compound 104
16-Deacetoxy-16β-propionyloxy-17S,20S-methanofusidic acid, Compound 105
16-Deacetoxy-16β-cyclohexylcarbonyloxy-17S,20S-methanofusidic acid, Compound 106
16-Deacetoxy-16β-(isopropionyloxy)-17S,20S-methanofusidic acid, Compound 107
16-Deacetoxy-16β-(4'-fluorobenzoyloxy)-17S,20S-methanofusidic acid, Compound 108
16-Deacetoxy-16β-furfuryloxy-17S,20S-methanofusidic acid, Compound 109
16-Deacetoxy-16β-ethoxy-17S,20S-methanofusidic acid, Compound 110
16-Deacetoxy-16β-(1',1',1'-trifluoroethoxy)-17S,20S-methanofusidic acid, Compound 111
16-Deacetoxy-16β-(methoxymethyl-17S,20S-methanofusidic acid, Compound 112
3-Dehydro-3β-bromo-17S,20S-methanofusidic acid, Compound 113

3-Dehydro-3β-chloro-17S,20S-methanofusidic acid, Compound 114 and their pharmaceutically acceptable salts and easily hydrolysable esters.

13. A stereoisomer of a compound of formula I or Ia in pure form; or a mixture of such stereoisomers.

14. A pharmaceutical composition comprising a compound according to claim 1, alone or together with a pharmaceutically acceptable, non-toxic carrier and/or auxiliary agent and optionally together with one or more other therapeutically active components.

15. A pharmaceutical composition according to claim 14 in the form of a topical preparation.

16. A pharmaceutical composition according to claim 15 in the form of an ointment.

17. A pharmaceutical composition according to any of claims 14–16 wherein said other therapeutically active component is selected from the group consisting of penicillins, cephalosporins, tetracyclines, rifamycins, erythromycins, linocomycin, clindamycin, fluoroquinolones and corticosteriods.

18. A method of treating a patient in need of antimicrobial treatment, the method comprising administering to said patient an effective amount of the composition of claim 14, optionally together or concomitantly with one or more other therapeutically active components.

19. A method according to claim 18 wherein said other therapeutically active component is selected from the group consisting of penicillins, cephalosporins, tetracyclines, rifamycins, erythromycins, lincomycin, clindamycin, fluoroquinolones and corticosteroids.

* * * * *